United States Patent [19]

Burgeson et al.

[11] Patent Number: 5,352,668
[45] Date of Patent: Oct. 4, 1994

[54] PRODUCT AND METHOD FOR IMPROVING KERATINOCYTE ADHESION TO THE DERMIS

[75] Inventors: Robnert E. Burgeson, Boston; Gregory P. Lunstrum, Portland, Oreg.; Patricia Rousselle, Lyons, France; Douglas R. Keene, Portland; M. Peter Marinkovich, Beaverton, both of Oreg.

[73] Assignee: The State of Oregon Acting By and Through The State Board of Higher Education on Behalf of Oregon Health Sciences University, Portland, Oreg.

[21] Appl. No.: 936,850

[22] Filed: Aug. 28, 1992

Related U.S. Application Data

[63] Continuation-in-part of Ser. No. 675,563, Mar. 26, 1991, abandoned.

[51] Int. Cl.$^5$ .......................... A61F 2/10; A61K 37/12; C07K 15/06; C07K 15/20
[52] U.S. Cl. .................................... 514/21; 530/350; 530/353; 530/842; 530/851; 623/15
[58] Field of Search ............... 530/350, 353, 395, 842, 530/851; 514/8, 21; 435/1; 623/15; 600/36

[56] References Cited

U.S. PATENT DOCUMENTS 4,829,000 5/0989 Kleinman et al. .................. 435/240

OTHER PUBLICATIONS

Journal of Investigative Dermatology, vol. 96, No. 4, issued Apr. 1991, Marinkovich et al., "Characterization of a Novel Laminin Isoform Produced by Human Keratinocytes in Vitro," see p. 551, col. 1, abstract No. 113.

E. Harris et al., "Protein purification methods, a practical approach," published 1989 by IRL Press (New York), see pp. 9, 10, 58–60, 62.

Alstadt et al., "Effect of Basement Membrane Entactin on Epidermal Cell Attachment and Growth," J. Invest. Dermatol. 88:55–59 (Jan. 1987).

Bächinger et al., "The Relationship of the Biophysical and Biochemical Characteristics of Type VII Collagen to the Function of Anchoring Fibrils," J. Biol. Chem. 265:10095–10101 (1990).

Boyce et al., "Cultivation, Frozen Storage, and Clonal Growth of Normal Human Epidermal Keratinocytes in (List continued on next page.)

*Primary Examiner*—Jeffrey E. Russel
*Attorney, Agent, or Firm*—Klarquist Sparkman Campbell Leigh & Whinston

[57] ABSTRACT

A purified protein kalinin is disclosed that provides adhesion between epidermal keratinocytes and the underlying dermis. Purified kalinin localizes to the anchoring filaments of basement membranes or human subepithelial skin, trachea, esophagus, cornea and amnion when such areas are probed with BM165 monoclonal antibody after localization. The protein has a molecular weight of approximately 400–460 kDa and exists in a cell-associated form (about 460 kDa) and two medium-associated forms (about 440 and 400 kDa, respectively). The cell-associated form comprises a 200-, a 155- and a 140-kDa subunit, all normally held together by disulfide bonds. The cell-associated form is subjected to extracellular processing to produce the two medium-associated forms, wherein, in the 440-kDa form, the 200-kDa subunit has been processed to a 165-kDa subunit and, in the 400-kDa form, the 155-kDa subunit has been processed to a 105-KDa subunit. The BM165 epitope is located on the 165-kDa subunit. Kalinin has a rotary-shadow image revealing an asymmetric rod 107-nm long having two globules at a first end and a single globule at an opposing end. A method is also disclosed for improving adhesion of transplanted keratinocytes to an underlying substrate, such as the human dermis, by optimizing production of kalinin from cultured keratinocytes, or by providing an exogenous source of kalinin between the keratinocytes and substrate.

9 Claims, 16 Drawing Sheets

OTHER PUBLICATIONS

Serum–Free Media," J. Tissue Culture Methods 9:83–93 (1985).

Carter et al., "Epiligrin, a New Cell Adhesion Ligand for Integrin α3β1 in Epthelial Basement Membranes," Cell 65:599–610 (May 17, 1991).

De Luca et al., "Polarized integrin mediates human keratinocyte adhesion to basal lamina," Proc. Natl. Acad. Sci. USA 6888–6892 (Sep. 1990).

Fine, "GB3 Antigen is an Accurate Marker of Only the Herlitz Subset of Junctional Epidermolysis Bullosa," Abstract, Clin. Res. 38(1) (1990).

Fine, "19–DEJ–1, A Hemidesmosome–Anchoring Filament Complex–Assocatied Monoclonal Antibody," Arch Dermatol 125:520–3 (1989).

Fisher, "Skin–The Ultimate Solution for the Burn Wound," New England J. of Medicine 311:466–467 (Aug. 16, 1984).

Gallico et al., "Permanent Coverage of Large Burn Wounds With Autologous Cultured Human Epithelium," The New England J. of Medicine 311:448–451 (Aug. 16, 1984).

Goldberg, "Is the lamina lucida of the basement membrane a fixation artefact?" European J. of Cell, Biol. 42:365–368 (1986).

Hancock, "Cultured keratinocytes and keratinocyte grafts," BMJ 299:1179–1180 (Nov. 11, 1989).

Heaphy et al., "The Human Cutaneous Basement Membrane–Anchoring Fibril Complex: Preparation and Ultrastructure," J. Invest. Dermatol. 68:177–186 (1977).

Keene et al., "Kalinin: A Novel Basement Membrane Component Implicated in keratinocyte Cell Adhesion," Abstract 2231, Basement Membrane Components (2218–2231) p. 401a.

Konter et al., "Adhesion molecule mapping in normal human skin," Arch Dermatol Res 281:454–462 (1989).

Lunstrum et al., "Identification of a New Basement Membrane Antigen which Localizes to the Lamina Lucida and Displays a Novel Tissue Distribution," Abstract 61, Cell Attachment to Extracellular Matrix I (56–71) p. 15a.

Lunstrum et al., "Large Complex Globular Domains of Type VII Procollagen Contribute to the Structure of Anchoring Fibrils," J. Biol. Chem. 261:9042–9048 (1986).

Morris et al., "The Tissue Form of Type VII Collagen Is an Antiparallel Dimer," J. Biol. Chem. 261:5638–5644 (1986).

Mortureux et al., "BM–600 Is Present in Normal Amniotic Fluid," Abstract, J. Invest. Dermatol. 95:481 (Oct. 1990).

O'Connor et al., "Grafting of Burns with Cultured Epithelium Prepared from Autologous Epidermal Cells," The Lancet, p. 75 (Jan. 10, 1981).

Phillips, "Cultured Skin Grafts–Past, Present, Future," Arch Dermatol 124:1035–1038 (Jul. 1988).

Rousselle et al., "Identification of a New Basement Membrane Antigen," Abstract in Western Connective Tissue Society Draft Program and Abstracts for Apr. 26–29, 1990, meeting, Santa Cruz, California.

Rousselle et al., "A Novel Basement Membrane Component Implicated in Keratinocyte Cell Adhesion," J. Cell Biol. 114:567–576 (1991).

Sakai et al., "Type VII Collagen Is a Major structural Companent of Anchoring Fibrils," J. Cell Biol. 103:1577–1586 (Oct. 1986).

Sakai et al., "Fibrillin, A New 35–kD Glycoprotein, Is a Component of Extracellular Microfibrils," J. Cell Biol. 103:2499–2509 (Dec. 1986).

Saksela et al., "Basal Lamina Components in Experimentally Induced Skin Blisters," J. Invest. Dermatol. 77:283–286 (1981).

Takashima et al., "Activation of Rabbit Keratinocyte Fibronectin Receptor Function In Vivo During Wound Healing," J. Invest. Dermatol. 86:585–590 (1986).

Thomas et al., "Cultured epithelia from junctional epidermolysis bullosa letalis keratinocytes express the main phenotypic characteristics of the disease," British J. Dermatol. 122:137–145 (1990).

Verrando et al., "The new basement membrane antigen recognized by the monoclonal antibody GB3 is a large size glycoprotein: modulation of its expression by retinoic acid," Biochemica et et Biophysica Acta 942:45–56 (1988).

Verrando et al., "Monoclonal Antibody GB3, a New Probe for the Study of Human Basement Membranes and Hemidesmosomes," Exp. Cell Res. 170:116–128 (1987).

Waikakul et al., "Application of Freeze–Dried Amniotic Membrane: A Control Trial at the Donor Site of Split–thickness Skin Grafting," Bulletin of the Hospital for Joint Diseases Orthopaedic Institute 50:27–34 (1990).

Woodley et al., "Burn Wounds Resurfaced by Cultured Epidermal Autografts Show Abnormal Reconstitution of Anchoring Fibrils," JAMA 259:2566–2571 (May 6, 1988).

J. Investigative Dermatology, vol. 92, No. 6, issued Jun. 1989, Fine et al, "Detection and Partial Characterization . . . ", pp. 825–830.

FIG. 3B
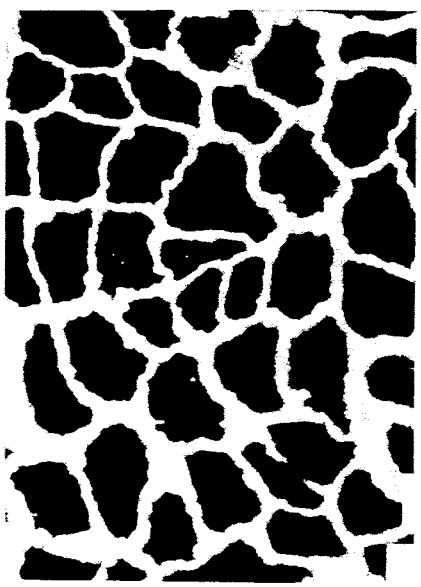
FIG. 3A
FIG. 3C
FIG. 3D

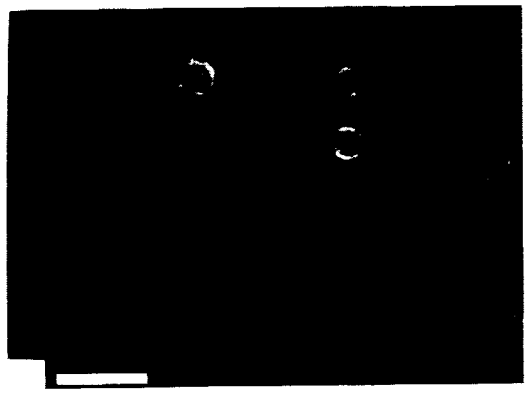
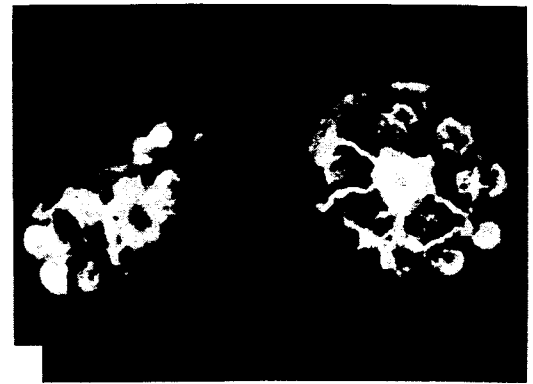
FIG. 6A                FIG. 6B
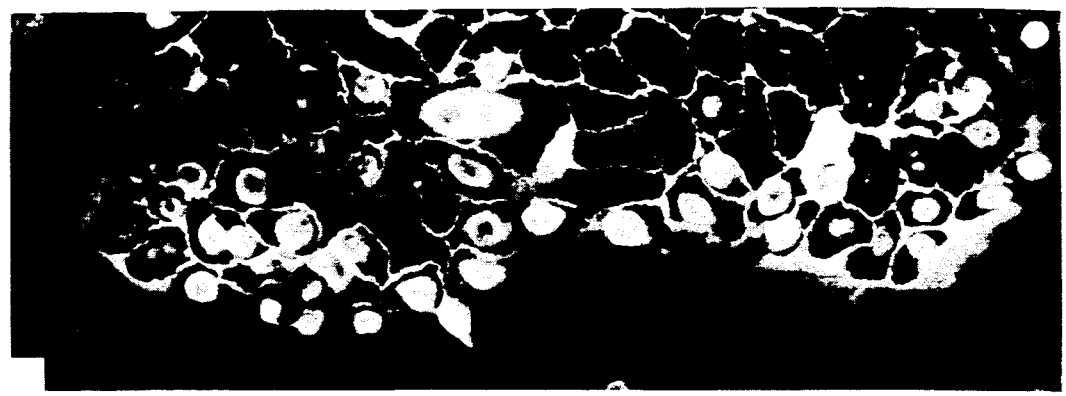
FIG. 6C
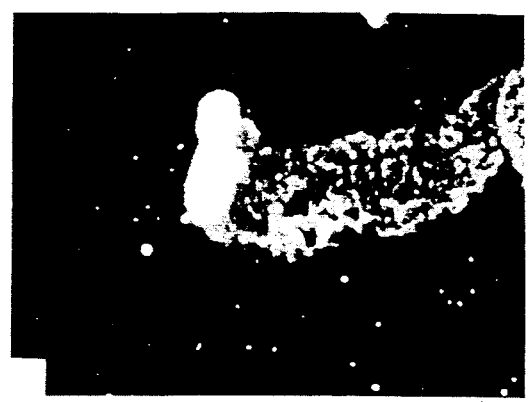
FIG. 6D                FIG. 6E

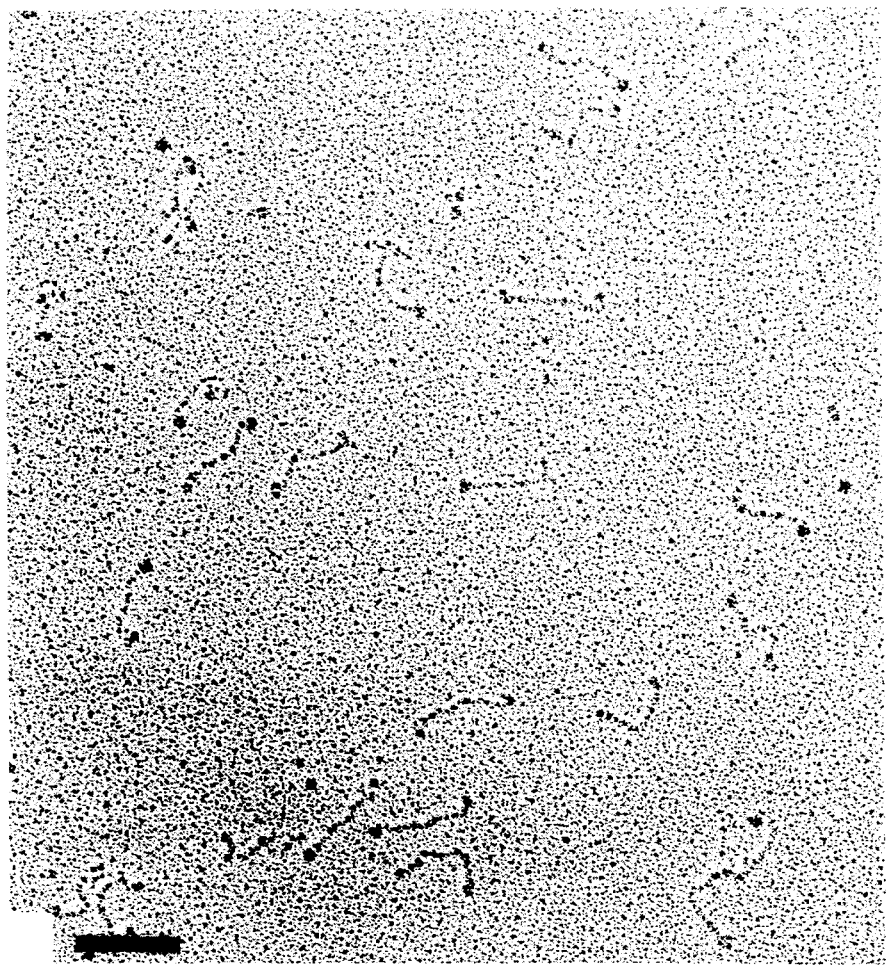
FIG. 8A
  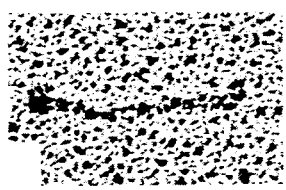  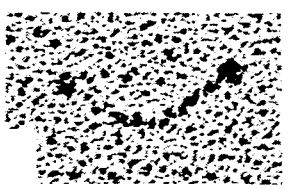
FIG. 8B            FIG. 8C            FIG. 8D
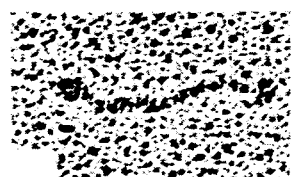  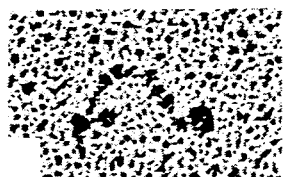  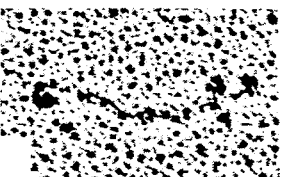
FIG. 8E            FIG. 8F            FIG. 8G

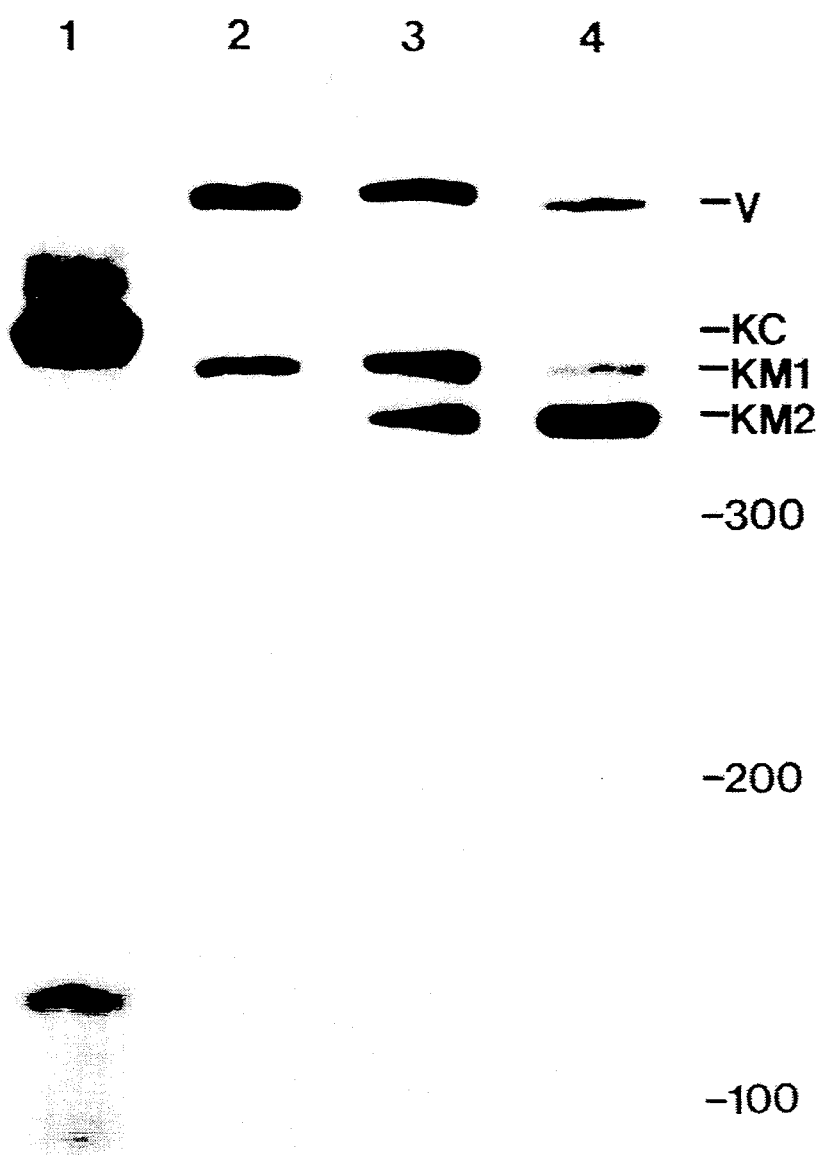

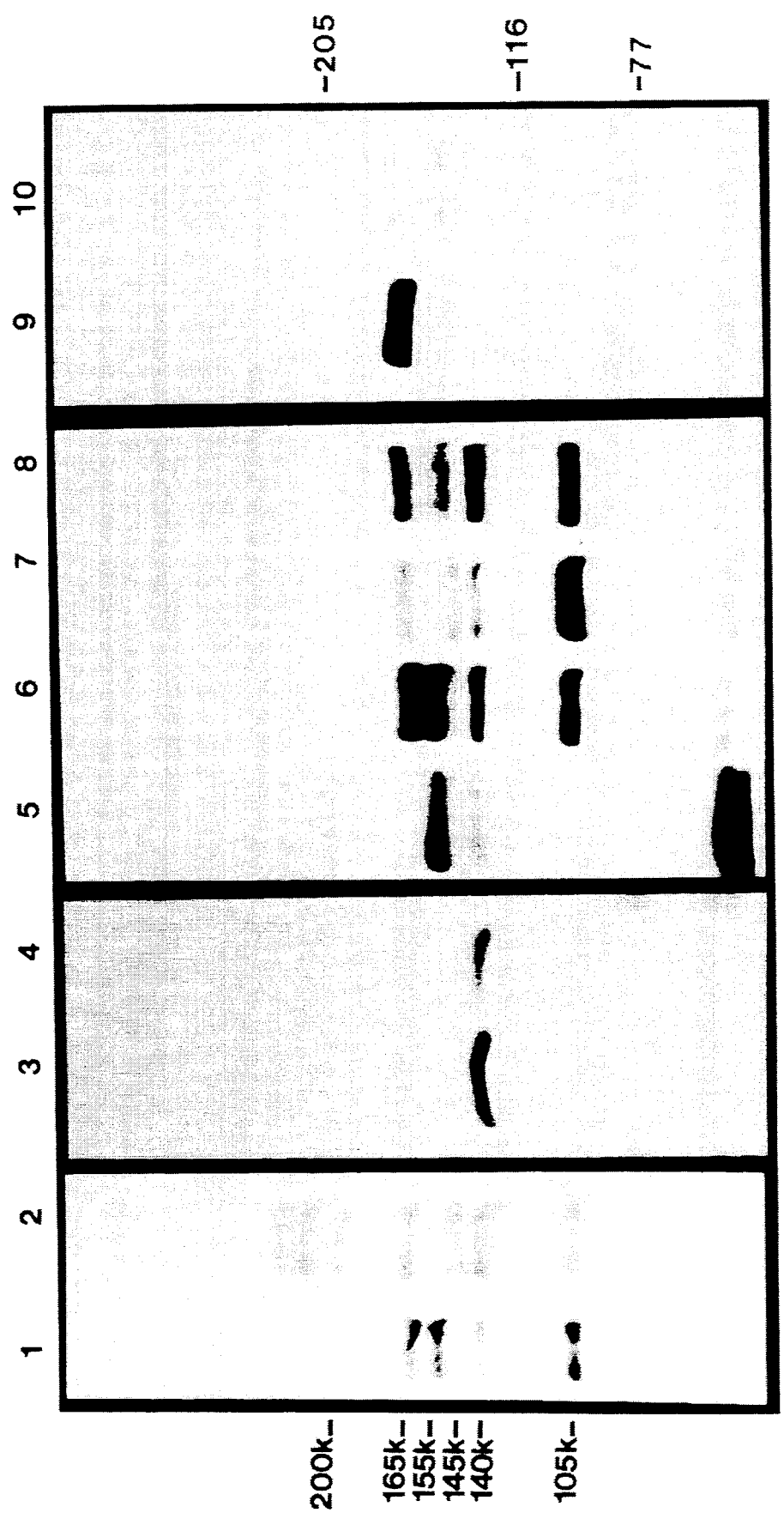

PRODUCT AND METHOD FOR IMPROVING KERATINOCYTE ADHESION TO THE DERMIS

ACKNOWLEDGEMENT

This invention was made with government support under grant number AR 35689 from the National Institutes of Health. Therefore, the U.S. Government has certain rights in this invention.

CROSS-REFERENCE TO RELATED APPLICATION

This application is a continuation-in-part of U.S. patent application Ser. No. 07/675,563, filed Mar. 26, 1991, now abandoned.

BACKGROUND OF THE INVENTION

1. Field of the Invention

This invention concerns a basement-membrane protein useful in adhering keratinocytes to the dermis. More specifically, this invention concerns a method of using this protein to enhance the success of skin transplants.

2. General Background of the Invention

The use of cultured epidermal grafts (keratinocyte grafts) to treat patients with life-threatening burns was first reported by O'Conner et al., *The Lancet* 1:75–78 (1981). Small skin biopsy specimens from burn patients were cultured in vitro, and the cultured autografts were placed on full thickness wounds on the arms of burn patients. The cultured keratinocytes successfully grew to cover the wounds in six weeks.

Subsequent attempts have been made to improve this method by modifying it to grow keratinocytes in serum-free medium. Others have suggested using composite cadaver skin allografts resurfaced with autologous cultured keratinocytes. Attempts have also been made to use different backing materials for the cultured cells or to vary the keratinocyte culture methodology. The results of cultured keratinocyte transplants, however, have often been disappointing.

One of the most useful applications for keratinocyte grafts has been in patients with burns damaging more than half of the body surface. Such patients have insufficient donor sites to provide enough split skin thickness grafts to resurface the area of the burn after surgical excision. Unfortunately, the results of keratinocyte autografting in these circumstances have been variable and disappointing.

Cultured epidermal grafts have been found to be significantly more fragile than normal skin and more prone to blistering. Woodley et al., *JAMA* 259:2566–2571 (1988). Some researchers have suggested that an abnormality in one or more connective tissue components within the autografts might explain the altered epidermal-dermal adherence observed clinically. The identity of that component, however, has remained obscure.

It is an object of this invention to identify and provide a therapeutically useful form of a connective tissue component that provides epidermal-dermal adherence.

It is another object of this invention to use such a therapeutically useful substance to enhance the adhesion of transplanted cultured keratinocytes to an underlying substrate, such as a mammalian or human dermis.

These and other objects of the invention will be understood more clearly by reference to the following detailed description.

SUMMARY OF THE INVENTION

The foregoing objects have been achieved by identification and production of a purified novel protein which is present in the anchoring filaments of the basement membranes of human subepithelial skin, trachea, esophagus, cornea and amnion. This novel protein, which has been named kalinin by its discoverers, has been found to provide adhesion between the human dermis and epidermis. This protein is also involved in the attachment of keratinocytes to solid substrates in vitro and to the basement membrane in vivo.

Kalinin exists in several forms having molecular weights in the range of about 400 to about 460 kDa. Kalinin separates on Western blots into distinct subunits after disruption of disulfide bonds in the intact molecule.

One form of kalinin is termed the "KC" form and is present in a "cell" fraction (associated with cells such as within cells or associated with a cell layer in cell cultures). The KC form has a molecular weight of about 460 kDa. When its disulfide bonds are disrupted, the KC form is separable into a 200-kDa subunit, a 155-kDa subunit, and a 140-kDa subunit.

Two other types of kalinin are termed the "KM1" and "KM2" forms which tend to accumulate in cell-culture medium bathing kalinin-producing cells under particular calcium concentrations. The KM1 form has a molecular weight of about 440 kDa and accumulates in media under low (0.035 mM) calcium concentrations. When its disulfide bonds are disrupted, KM1 is separable into a 165-kDa subunit, a 155-kDa subunit, and a 140-kDa subunit. The KM2 form has a molecular weight of about 400 kDa and accumulates in medial under a high (1.0 mM) calcium concentration. When its disulfide bonds are disrupted, KM2 is separable into a 165-kDa subunit, a 140-kDa subunit, and a 105-kDa subunit. The 140-kDa subunits of KC, KM1, and KM2 appear to be identical. The 165-kDa subunit of KM1 and KM2 appear to be derived from extracellular processing of the 200-kDa subunit of KC. The 155-kDa subunit of KC appears to be identical to the 155-KDa subunit of KM1. Thus, during conversion of KC to KM1, the 200-kDa subunit is processed to 165 kDa and, during conversion of KM1 to KM2, the 155-kDa subunit is processed to 105 kDa.

The epitope which is recognized by monoclonal antibody BM165 is identified on the 165-kDa subunit when the blots are probed with antibody BM165. The antibody BM165 also immunoreacts with a 650-kDa protein isolated from keratinocyte cell-culture medium. This 650-kDa protein is a novel variant of laminin possessing a 190-kDa subunit including an epitope recognized by the BM165 antibody.

Rotary shadow imaging of the 440-kDa form of kalinin reveals an asymmetric 107-nm long rod having two small globules at a first end and a single large globule at the opposite end. The 400-kDa form appears to lack the second small globule at the first end. Kalinin has been found to be absent in the dermal-epidermal junction of humans with diseases such as junctional epidermolysis bullosa, in which the epidermis separates from the underlying dermis.

Immunolocalization of kalinin to human skin demonstrates that this antigen is the ultrastructural element known as the anchoring filament. The rod-like shape and the length demonstrated by rotary shadowing of kalinin is also consistent with this role. The finding that most kalinin localizes to the lamina densa following antibody-induced rupture of the dermal-epidermal junction suggests that the BM165 antibody epitope lies near the region of the kalinin molecule responsible for binding to the hemidesmosome. The opposite end of the antigen appears to be buried in the lamina densa.

The invention also encompasses a method of improving adhesion of transplanted keratinocytes to an underlying substrate by providing an amount of kalinin between the keratinocytes and substrate which is greater than the amount produced naturally by keratinocytes. This increased amount of kalinin can be supplied by applying exogenous purified kalinin to the substrate such as a wound surface or to the basal surface of a confluent layer of cultured keratinocytes prior to placing the layer on a graft site.

According to another aspect of the present invention, as an alternative to applying kalinin to cultured keratinocyte cells prior to transplantation, the cultured keratinocytes can be induced to increase their basal levels of kalinin production to supra-physiologic levels by exposing the cells to growth promoters such as cytokines. Alternatively, according to yet another aspect of the present invention, keratinocytes are monitored during culturing to determine the time when they are actively producing kalinin; the keratinocytes are transplanted to a substrate before active kalinin production by the cells declines significantly.

BRIEF DESCRIPTION OF THE DRAWINGS

FIG. 3A is a photomicrograph of a confluent layer of cultured keratinocytes stained with BM165 antibody, the small bar indicating a length of 20 nm.

FIG. 3B is a photomicrograph similar to FIG. 3A wherein the confluent keratinocyte culture was stained with control media.

FIG. 3C is a photomicrograph similar to FIG. 3A wherein the transmission electron micrograph section is taken through the cell layer parallel to the culture substrate, the black bar indicating a length of 20 nm.

FIG. 3D is a photomicrograph similar to FIGS. 3A–C in which the cells are removed from the substrate with EDTA before staining with the BM165 antibody.

FIG. 6A is a photomicrograph of cultured keratinocytes that were exposed to the BM165 monoclonal antibody after 6 hours, the bar representing a length of 50 μm.

FIG. 6B is a photomicrograph similar to FIG. 6A in which the cultured keratinocytes were exposed to the BM165 antibody after 24 hours in culture.

FIG. 6C is a photomicrograph similar to FIG. 6A in which the keratinocytes were exposed to BM165 antibody after 48 hours in culture.

FIG. 6D is a photomicrograph similar to FIG. 6B illustrating substrate labeling along the paths of migrating keratinocytes.

FIG. 6E is a figure similar to FIG. 6D.

FIG. 8A is a photograph showing rotary shadow analysis of the BM165 antigen following affinity purification, the bar representing a length of 100 nm.

FIG. 8B, FIG. 8C and 8D are higher magnification photographs of the rotary shadow images of FIG. 8A.

FIG. 8E, FIG. 8F, and FIG. 8G are further high magnification views of the rotary shadow analysis of FIG. 8A.

FIGS. 10A–10B depict results of immunoprecipitation of kalinin from cultured keratinocytes grown in different calcium concentrations, followed by electrophoresis on acrylamide gels.

FIG. 12 is a comparison of cell-associated, medium-associated, and tissue-associated forms of kalinin identified by Western blotting.

DETAILED DESCRIPTION OF PREFERRED EMBODIMENTS

Figure 9:
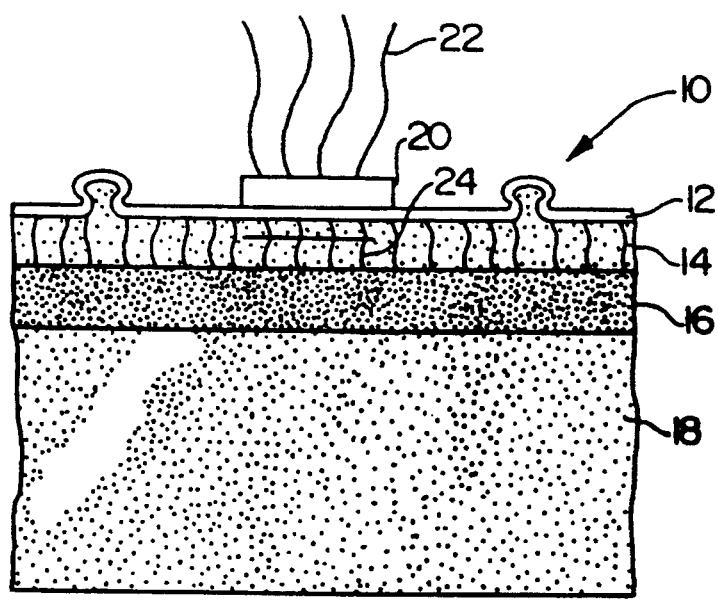
FIG. 9 is a schematic diagram of the ultrastructure of the basement membrane region at the dermal-epidermal junction of human skin.

The ultrastructure of the basement membrane at the epidermal-dermal junction is shown schematically in FIG. 9, which depicts the lower part of a basal keratinocyte 10 having a plasma membrane 12 that seats on a lamina lucida 14, subadjacent lamina densa 16, and dermis 18. A hemidesmosome 20 is depicted at the basal portion of keratinocyte 10 on plasma membrane 12. Tonofilaments 22 insert into the hemidesmosome 20 and extend into the cytoplasm. Anchoring filaments 24 arise from the plasma membrane beneath the attachment plaque of hemidesmosome 20. The filaments traverse the lamina lucida 14 and connect the basal plasma membrane 12 with the lamina densa 16, and are most numerous in the region of the hemidesmosome. Anchoring fibrils 26, in contrast, are short curved structures, with an irregularly spaced cross banding of their central portions, which fan out at either end. The distal part of fibrils 26 inserts into the lamina densa while the proximal part terminates in the papillary dermis or loops around to merge into the lamina densa.

The present invention concerns a protein associated with the anchoring filaments 24, which performs an important function in adhering the dermis to the epidermis.

The ultrastructure of the anchoring fibril network suggests that it secures the basement membrane to the underlying dermis. Susi et al., J. Cell Biol 34:686–690 (1967); Kawanami et al., Am. J. Pathol. 92:389–410 (1978). This hypothesis is supported by observations that individuals with recessive dystrophic epidermolysis bullosa lack anchoring fibrils (Briggaman et al., J. Invest. Dermatol. 65:203–211 (1975); Leigh et al., J. Invest. Dermatol. 90:612–639 (1988); Bruckner-Tuderman et al., J. Invest. Dermatol. 93:3–9 (1989)) and suffer from spontaneous separation of the epidermal basement membranes from the subadjacent stroma.

The molecular heterogeneity of the dermal-epidermal junction is reflected by the presence of several glycoproteins localized to this zone. Hemidesmosomes, for example, contain several proteins having $M_r$ values from 165,000–240,000. Mutasim et al., J. Invest. Dermatol. 92:225–230 (1989); Westgate et al., J. Invest. Dermatol. 81:149–153 (1985); Regnier et al., J. Invest. Dermatol. 85:187–190 (1985); Jones et al., Cell Motil. Cytoskel. 6:560–569 (1986); Stanley et al., J. Invest. Dermatol. 82:108–111 (1984); Labib et al., J. Immunology 136:1231–1235 (1986); and Mueller et al., J. Invest. Dermatol. 92:33–38 (1989) An integrin termed $\alpha 6\beta 4$ has also been recently localized to the external region of the hemidesmosome by Stepp et al., Proc. Nat. Acad. Sci. USA 87:8970–8974 (1990). The anchoring fibrils themselves include lateral unstaggered aggregates of type VII collagen described by Sakai et al., J. Cell Biol. 103:1577–1586 (1986); and Lunstrum et al., J. Biol. Chem. 262:13706–13712 (1987).

In addition to these known proteins, several antibodies have been found which recognize antigens unique to the dermal-epidermal junction. An example is the murine monoclonal antibody 19-DEJ-1 which recognizes an unknown antigen absent from the basement membrane of skin from patients with epidermolysis bullosa. Fine, Arch. Dermatol. 124:713–717 (1988). The antigen detected by 19-DEJ-1 is unknown and only partially characterized.

The structural relationship among proteins of the hemidesmosomes, the basement membrane constituents, and type VII collagen in anchoring fibrils has not been clearly elucidated. Some researchers have suggested an association between anchoring fibrils and the hemidesmosomes based on ultrastructural analyses in which hemidesmosomes are found to regenerate only on sites along denuded basement membranes directly over anchoring fibrils Gipson, J. Cell Biol. 97:849–857 (1983); Susi et al., J Cell Biol. 34:686–690 (1967); and Ellison et al., J. Cell Sci. 72:163–172 (1984). Hemidesmosomes and anchoring fibrils have also been observed to appear simultaneously during fetal development and wound healing. Gipson et al., Dev. Biol. 126:253–262 (1988); and Smith et al., J. Invest. Dermatol. 90:480–485 (1988). Published models for the structure of anchoring fibrils include the prediction that direct contact between type VII collagen and the hemidesmosome is unlikely because the NC-1 domain of type VII collagen has a diameter of only 50 nm and is not large enough to span the entire basement membrane which is wider than 50 nm. Hence, other proteins likely link type VII collagen to the hemidesmosomal proteins. Lunstrum et al., J. Biol. Chem. 262:13706–13712 (1987); Keene et al., J. Cell Biol. 104:611–621 (1987); and Bächinger et al., J. Biol. Chem. 265:10095–10101 (1990).

The present inventors describe herein a protein according to the present invention that is associated with anchoring filaments. This protein is further characterized by ultrastructural location and tissue distribution. The protein has been purified and its filamentous conformation determined by shadow imaging. Finally, this newly purified protein is shown to be necessary for the in vitro attachment of keratinocytes to plastic or glass substrates and to the basement membrane in vivo.

1. Source of Immunogen

Kalinin is localized using the monoclonal antibody BM165, which was prepared using a "BM165 immunogen."

The BM165 immunogen was derived from an extract of human amnion, prepared as follows. Collagenase extraction and purification of the NC-1 globular domain of type VII collagen from human amnion has been described previously. Bächinger et al., J. Biol. Chem. 265:10095–10101 (1990). During one step of this purification, the extract is incubated with DEAE-cellulose (DE52, Whatman) in a low salt buffer (2M urea, 25 mM NaCl, 5 mM EDTA and 50 mM Tris-HCl, pH 7.8). The unbound fraction was used in the further purification of the NC-1 domain. The DEAE-cellulose was washed with an equal volume of buffer containing 0.2M NaCl and the eluted material was isolated after centrifugation at 17,000×g for 60 min. The sample was concentrated 10-fold by ammonium sulfate precipitation (50% saturation) and equilibrated in PBS (phosphate-buffered saline) by dialysis. The resulting complex mixture of proteins served as an immunogen in the preparation of hybridomas.

2. Keratinocyte Cell Culture

Human foreskin keratinocytes were prepared according to the published procedures of Boyce et al., *J. Tiss. Cult. Meth.* 9:83–93 (1985), which are incorporated herein by reference. Cells were grown in Keratinocyte Growth Medium (KGM) containing 0.15 mM $CaCl_2$ and subcultured according to the manufacturer's instructions (Clonetics). For most immunocytochemical experiments, first- or second-passage cells were grown in glass or plastic chamber slides (Lab-Tek) or on glass cover slips to approximately 80 percent confluency. For large-scale collection, spent-media cells were grown in 150-$cm^2$ tissue culture dishes and fed three times per week with 15 mL fresh media.

3. Affinity Purification of the BM165 Antigen

Media collected from growing keratinocytes was clarified by centrifugation at 2,000×g for 10 min. Endogenous protease activity was minimized by the addition of EDTA, PMSF (phenylmethylsulfonyl fluoride) and N-ethylmaleimide to final concentrations of 5 mM, 50 uM, and 50 uM, respectively. The media was sterilized by filtration and either processed immediately or stored frozen at −20° C. until use.

BM165 monoclonal antibodies (mAbs) were conjugated to CNBr-activated Sepharose 4B (Pharmacia LKB, Inc.), at 1 mg of antibody per mL of resin, as described by the manufacturer. Keratinocyte medium (1–2 liters) was passed through a 15-mL column of the conjugated antibodies and the column was washed with PBS. The BM165 antigen was eluted with 1M acetic acid and fractions were monitored for absorbance at 280 nm. Pooled fractions were treated with diisopropylfluorophosphate (5 ug/mL) and dialyzed against appropriate buffers for further analysis.

To perform SDS-PAGE (sodium dodecyl sulfate-polyacrylamide gel electrophoresis) of the eluted fractions, samples of the fractions were separated on 3–5% gradient gels before reduction and on 5% gels after reduction with β-mercaptoethanol. In addition to high molecular weight pre-stained standards (Biorad), the NC-1 domain of disulfide-bonded type VII collagen ($M_r$=450,000 daltons), reduced NC-1 domains ($M_r$=150,000 daltons) and reduced fibrillin ($M_r$=350,000 daltons) (Sakai et al., *J. Cell Biol.* 103:1577–1586 (1986)) were used in determining $M_r$ scales.

4. Tissue Preparation

Enbloc immunolocalization of antigens was performed as previously described by Keene et al., *J. Cell Biol.* 104:611–621 (1987), with some modifications as follows:

Human neonate foreskins collected shortly after circumcision were cut into 0.5 mm×1 mm blocks, all including epithelium, and washed for two hours in phosphate buffered saline (PBS), pH 7.4 at 4° C., rinsed in several changes of PBS over 6 hours, then incubated overnight at 4° C. in 1-nm gold-conjugated secondary antibody (Janssen Life Sciences Products, Piscataway, N.J.) diluted 1:3 in PBS containing 1.0% BSA (bovine serum albumin). Following washing, the foreskin tissues were submersed in ice-cold silver intensification solution (Janssen Life Sciences Products, Piscataway, N.J.) for 15 minutes, then rapidly warmed to room temperature. After allowing silver to precipitate upon the 1-nm gold particles for seven minutes at room temperature, the tissues were rinsed several times over a 15-minute period with water, then rinsed with 0.1M cacodylate buffer at pH 7.4. The tissues were finally fixed in 0.1-M cacodylate-buffered 1.5%/1.5% glutaraldehyde/paraformaldehyde, pH 7.4, dehydrated in a graded series of ethanol dilutions, exposed to propylene oxide, and embedded in Spurrs epoxy.

Figure 2A:
FIG. 2A is a photomicrograph of the dermal-epidermal junction in human skin showing the ultrastructural features of this region, the bar representing a length of 100 nm.

Control antibodies used included those recognizing elastin (produced and provided by Dr. Lynn Sakai), collagen type IV (Sakai et al, *Am. J. Pathology* 108:310–318 (1982)), and collagen type VI (Keene et al, *J. Cell. Biol.* 107:1995–2006 (1988)). One sample of skin was fixed for 30 minutes in ice-cold acetone, rinsed in buffer, further fixed in 3%/3% aldehydes and 1% $OsO_4$, then dehydrated in acetone prior to embedding in Spurrs epoxy in order to demonstrate the presence of anchoring filaments (FIG. 2A).

5. Electron Microscopic Examination

For examination of normal cell ultrastructure prior to antibody treatment, human keratinocyte cultures were grown on glass coverslips and fixed in 0.1-M cacodylate-buffered 1.5%/1.5% glutaraldehyde/paraformaldehyde, 1.0% $OsO_4$. The cultures were dehydrated in a graded ethanol series, then either embedded directly in Spurrs epoxy for transmission electron microscopy (TEM), or critical-point dried and sputter-coated for scanning electron microscopy (SEM) as previously described. Keene et al., *J. Cell. Biol.* 107:1995–2006 (1988).

TEM immunoelectron microscopy was performed on keratinocytes grown on 8-well permanox culture flasks using an identical protocol as that described above for tissues, except that (a) the incubation time in primary antibody was four hours at room temperature; (b) the secondary antibody was conjugated to 5-nm gold and diluted 1:3 in BSA buffer (20 mM Tris-HCl, 0.9% NaCl, 1 mg/mL BSA, 20 mM $NaN_3$); and (c) the silver-intensification procedure was omitted.

Keratinocytes grown on glass coverslips and observed by SEM following exposure to antibody were treated identically, except they were critical-point dried from liquid $CO_2$ following dehydration in ethanol.

For routine TEM examination, 60- to 90-nm thick sections were cut on a Reichert ultramicrotome using diamond knives. The sections were contrasted in uranyl acetate and Reynolds lead citrate (Reynolds, *J. Cell Biol.* 17:208–215 (1963)) and examined using a Philips 410 LS TEM instrument operated at 60 kV. For routine SEM examination, samples were sputter-coated with a minimum amount of gold-palladium and observed in the upper stage of a scanning electron microscope (Model DS130; International Scientific Instruments, Inc., Milpitas, Calif.) operated at 10 kV, using a spot size of 3–10 nm.

6. Other Techniques

Methods including Western blotting, rotary-shadow analysis and length measurements have been detailed elsewhere. Morris et al., *J. Biol. Chem.* 261:5638–5644 (1986); Lunstrum et al., *J. Biol. Chem.* 261:9042–9048 (1986); and Bächinger et al., *J. Biol. Chem.* 265:10095–10101 (1990).

Rotary shadowing of molecules was accomplished using a modification of standard techniques described by Shotton et al., *J. Mol. Biol.* 131:303–329 (1979) and Tyler et al., *J. Ultrastruct. Res.* 71:95–102 (1980). Samples in 0.15-M carbonate buffer, pH 7.4, were diluted with glycerol to a final concentration of 70%. Then, 100 μL of solution were sprayed through an airbrush at an acute angle onto freshly cleaved 6-mm diameter mica discs. Droplet diameters were 50–200 μm. Samples were dried in an evaporator at $10^{-6}$ Torr. Platinum wire was wrapped around the carbon electrodes and the sample was placed on the stage and rotated at 100 rpm. At high voltage, the platinum was evaporated to completion at a 6-degree angle from the mica surface. The stage was then tilted 90 degrees relative to a carbon source and the chamber was evacuated. A 50-Å layer of carbon was evaporatively deposited onto the surface of the mica to form a "carbon replica." The carbon replica was immediately floated off the mica by carefully immersing the carbon-coated mica in double-distilled water. The carbon replicas were mounted onto 400-mesh grids. The replicas were examined using a transmission electron microscope at 80 kV with a 30 μm objective aperture.

7. BM165 Hybridoma and Monoclonal Antibody Preparation

Hybridomas were prepared and screened by indirect immunofluorescence as previously described. Sakai et al., *J. Cell Biol.* 103:1577–1586 (1986). The BM165 mAb, an IgG$_1$, was purified from cell culture supernatants as described elsewhere, Keene et al., *J. Cell Biol.* 113:971–978 (1991). Several monoclonal antibodies were provided by Dr. Eva Engvall of the La Jolla Cancer Research Foundation, which included the following: 11D5 mAb (Engvall et al., *Cell Regulation* 1:731–740 (1990)), 4C7 mAb specific for the laminin A chain (Engvall et al., *J. Cell Biol.* 103:2457–2465 (1986)), and 4E10 mAb specific for the laminin B chain (Wewer et al., *J. Biol. Chem.* 258:12654–12660 (1983)). Rabbit polyclonal antiserum against mouse laminin was obtained from Sigma Chemical Company of St. Louis, Mo.

Monoclonal antibodies were raised to a mixture of partially purified proteins originally extracted from human amnion by collagenase digestion as described for the isolation of the type VII collagen NC-1 domain. Bächinger et al., *J. Biol. Chem.* 265:10095–10101 (1990). The resulting hybridomas were screened by indirect immunofluorescence for localization to the dermal-epidermal zone, but not to the vascular basement membrane zone, of human fetal foreskin. Selected hybridomas were rescreened by Western blotting of the immunogen and protein extracts containing known basement membrane components. Hybridomas that did not recognize known basement membrane components were retained for further study.

Figure 1A:
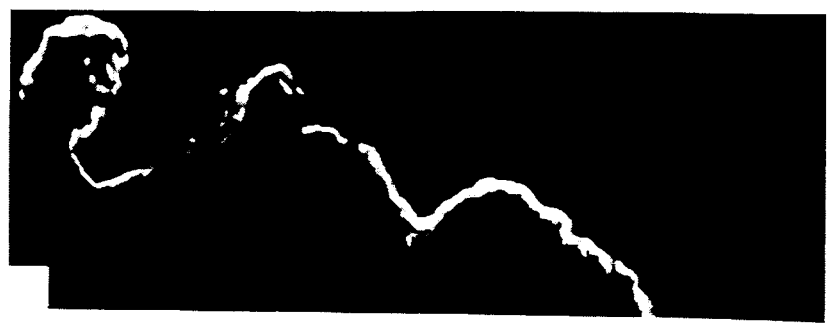
FIG. 1A is a photomicrograph showing the indirect immunofluorescent localization of the BM165 antigen in human foreskin.
Figure 1B:
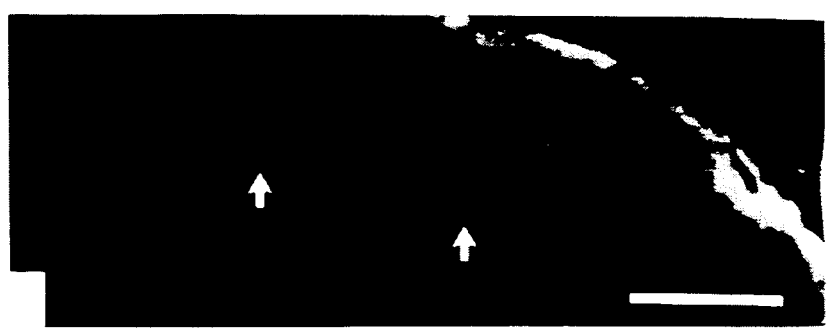
FIG. 1B is a photomicrograph similar to FIG. 1A wherein the frozen section was stained with media from unfused myelomas.

One of the aforesaid screenings produced two hybridomas that appeared to recognize the same unique protein. One of these, termed BM165, was used for the studies reported here. The monoclonal antibody produced by the BM165 hybridoma, also termed BM165, specifically identifies the dermal-epidermal junction basement membrane zone of skin, but shows no reactivity to the basement membranes of the vasculature or surrounding nerves (FIG. 1).

8. Tissue Distribution of BM165 Immunoreactivity

The tissue distribution of BM165 mAb reactivity is shown in Table I. All of the subepithelial regions of skin, trachea, esophagus, cornea and amnion exhibited crisp, brilliant, continuously linear fluorescence. The tissue distribution of fluorescence directly paralleled the occurrence of hemidesmosomes and anchoring fibrils, with the exception of occasional and weak staining of the intestinal smooth muscles. No BM165 mAb reactivity was observed in tissue from human kidney, blood vessels, nerve, and cartilage.

TABLE I

Tissue Distribution of Antigen Recognized by BM165 mAbs As Determined by Indirect Immunofluorescence

| Tissue | Result |
| --- | --- |
| Skin, subepithelial | + |
| Trachea, subepithelial | + |
| Esophagus, subepithelial | + |
| Cornea, subepithelial | + |
| Amnion, subepitelial | + |
| Intestinal smooth muscle | ± |
| Kidney | − |
| Blood vessels | − |
| Nerve | − |
| Cartilage | − |

The BM165 mAb was then used to localize the corresponding antigen within the dermal-epidermal basement membrane of human foreskin. Primary antibody was localized using secondary antibody conjugated to 1 nm gold, which was visualized by silver enhancement. The use of 1-nm gold was necessary due to the limited penetration of the basement membrane by a 5-nm gold-conjugated secondary antibody.

Figure 2B:
FIG. 2B is a photomicrograph similar to FIG. 2A showing localization of BM165 monoclonal antibody to the anchoring filaments of the dermal-epidermal basement membrane.
Figure 2C:
FIG. 2C is a photomicrograph similar to FIG. 2B but at a lower magnification, showing BM165 antibody labeling along a continuous stretch of intact skin, the bar representing a length of 200 nm.

This procedure localized the BM165 antigen to the anchoring filaments, just below the basal dense plate of hemidesmosomes (FIG. 2B and 2C). No labeling of the anchoring filaments was seen when an antibody of irrelevant specificity was employed as the primary antibody (data not shown). Some additional label was observed along the lamina densa (FIG. 2C), but the majority of the label appeared beneath the hemidesmosomes. Small amounts of gold deposits were also seen beneath the dermal side of the lamina densa.

Figure 2D:
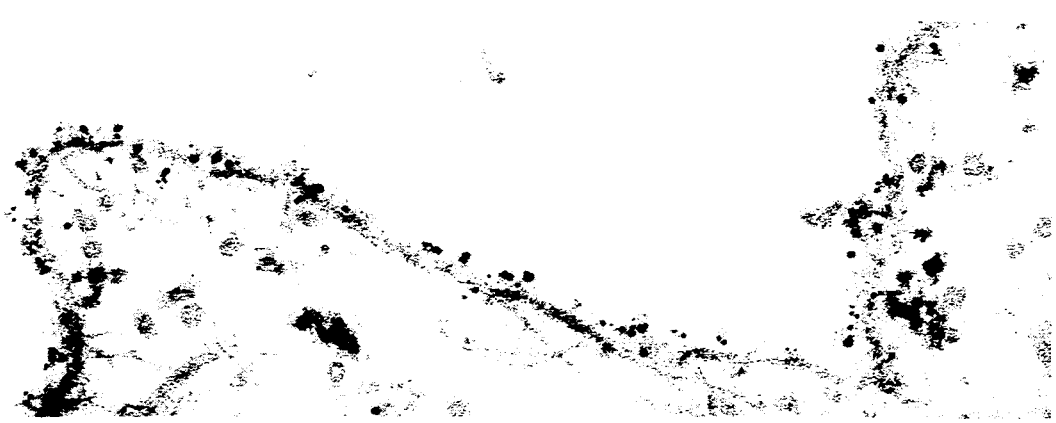
FIG. 2D is a photomicrograph similar to FIG. 2C showing BM165 antibody labeling along the basement membrane in a region where the antibody has induced epidermal detachment.

Throughout these experiments, extensive, often complete de-epithelization of skin samples during incubation with the primary antibody was commonly observed. This was entirely outside the inventors' considerable experience with use of antibodies to type-IV and type-VII collagens. The regions of unsplit basement membrane shown in FIGS. 2B and C comprised regions that are relatively distant from the tissue edge. Near the tissue edge, where the antibody concentration was highest and the epidermis had separated from the basement membrane, very strong labeling was seen uniformly along the lamina densa, at what had been the cell interface (FIG. 2D). Some label was seen still associated with the extracellular face of the hemidesmosome, but this was relatively rare (not shown).

Although the present inventors do not desire to be bound by theories and the limitations of scientific knowledge, the orientation of the molecular elements of the basement membrane zone seen by conventional microscopy may be entirely artifactual. Electron microscopic examination of rat incisor, tongue and gingiva prepared by rapid-freezing and freeze-substitution demonstrate a homogenous 25–100 nm thick electron-dense basement membrane completely lacking a lamina lucida. Goldberg et al., *Eur. J. Cell Biol.* 42:365–368 (1986). One of the present inventors has made the same observation with the dermal-epidermal junction of human skin. Therefore, it is possible that the lamina lucida is an artifact resulting from the cell shrinking away from the basement membrane, and the lamina densa is the residue of the entire basement membrane. If this is the case, it is likely that kalinin is situated entirely within the basement membrane, with only one end concentrated at the site where the hemidesmosome contacts the basal lamina. The anchoring filaments would then reflect those species within the basal lamina that are strongly bound to the hemidesmosome and become taut and linear as they are pulled from the basement membrane as the cell shrinks away.

9. Kalinin Localization in Cell Cultures

The BM165 mAb was used to visualize the corresponding antigen in keratinocyte cultures. As shown in FIG. 3A, when applied to the top surface of a layer of confluent cells, the antibody localized to the surface of the plastic substrate between the cultured cells (compare to FIG. 3C, which is taken through the cell layer parallel to the culture substrate). No intracellular fluorescence was observed. This unusual localization could not be duplicated with antibodies to type-IV collagen (Sakai et al., *Am. J. Pathology* 108:310–318 (1982)), to laminin, or to type-VII collagen (Sakai et al., *J. Cell Biol.* 103:1577–1586 (1986)) (data not shown).

Such localization of BM165 mAbs was not observed when antibodies of the same immunological subtype, but of irrelevant specificity were used (data not shown). The antigen was also present on the substrate underneath the cells as shown by strong fluorescence of the entire plastic substrate after removal of the cells with 10 mM EDTA (FIG. 3D).

Figure 4A:
FIG. 4A is a photomicrograph of a continuous subcellular matrix in a keratinocyte culture that was grown to near confluency, then washed with PBS (phosphate-buffered saline) and incubated with BM165 monoclonal antibody followed by 5-nm gold-conjugated secondary antibody prior to fixation.
Figure 4B:
FIG. 4B is a photomicrograph similar to FIG. 4A in which the keratinocytes were grown to near confluency and fixed immediately without BM165 antibody staining.
Figure 4C:
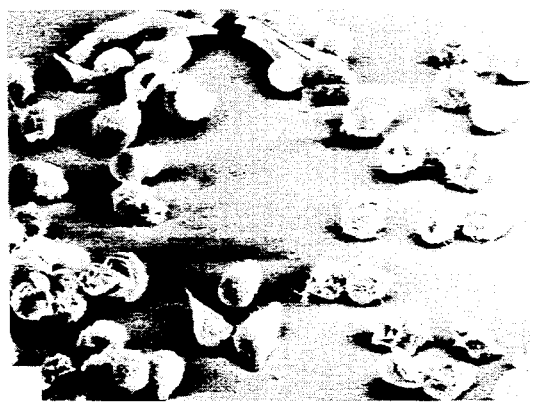
FIG. 4C is a scanning electron micrograph of cells prepared as in FIG. 4A.

The BM165 antigen was also localized along a continuous subcellular matrix in keratinocyte cell culture, as shown in FIGS. 4A–4D. Keratinocytes were grown to near confluence and either fixed immediately (FIGS. 4B and 4D) or washed with PBS and incubated with BM165 mAb (50 μg/mL) followed by 5-nm gold-conjugated secondary antibody prior to fixation (FIGS. 4A and 4C). Electron microscopic examination of the antigen in keratinocyte cultures revealed a linear deposition of immunogold conjugates uniformly across the substrate upon a fine electron-dense feltwork (FIG. 4A). The feltwork continued under the cell, but was often unlabeled. Thickenings could occasionally be seen along the keratinocyte plasma membrane that resembled immature hemidesmosomes (FIG. 4B), similar to structures observed by others. Compton et al., *Lab. Invest.* 60:600–612 (1989).

Figure 4D:
FIG. 4D is a scanning electron micrograph of a confluent culture prepared as in FIG. 4B.
Figure 5A:
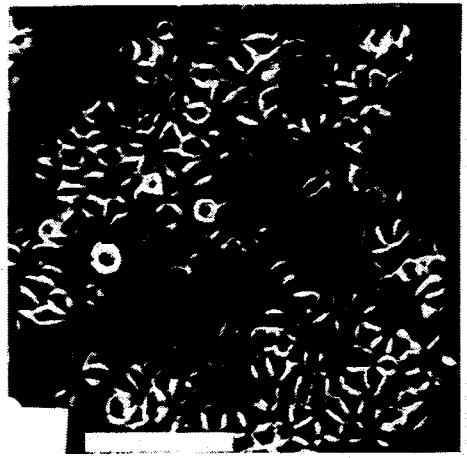
FIG. 5A is a photomicrograph of keratinocytes grown to 75–80% confluency, then washed and treated with PBS and photographed 10 minutes after treatment; the bar represents 20 μm.
Figure 5B:
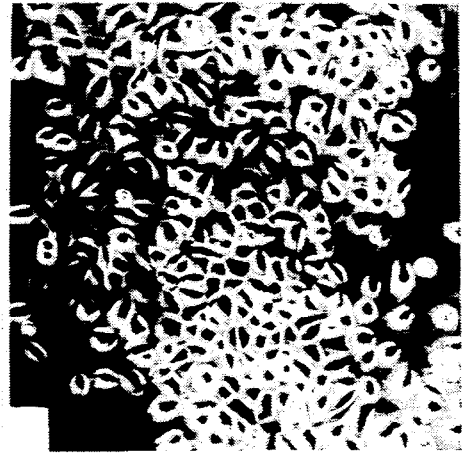
FIG. 5B is a photomicrograph similar to FIG. 5A in which the cells were photomicrographed 60 minutes after PBS treatment.
Figure 5C:
FIG. 5C is a photomicrograph similar to FIG. 5A in which the cells were washed with PBS and treated with 50 μg/mL BM165 mAb then photographed after 10 minutes.
Figure 5D:
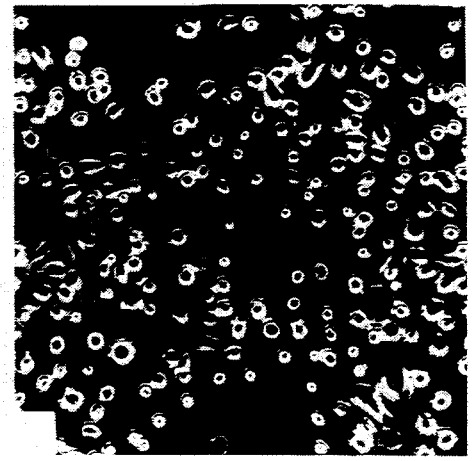
FIG. 5D is a photomicrograph similar to FIG. 5C, obtained 60 minutes after exposure to BM165 monoclonal antibody.
Figure 5E:
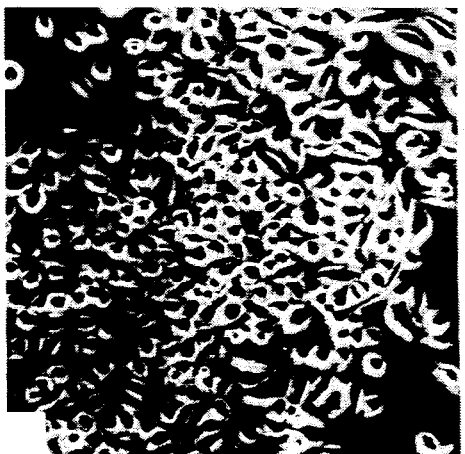
FIG. 5E is a photomicrograph similar to FIG. 5A in which the cells were washed with PBS and treated with 10 mM EDTA, photographed 10 minutes after treatment.
Figure 5F:
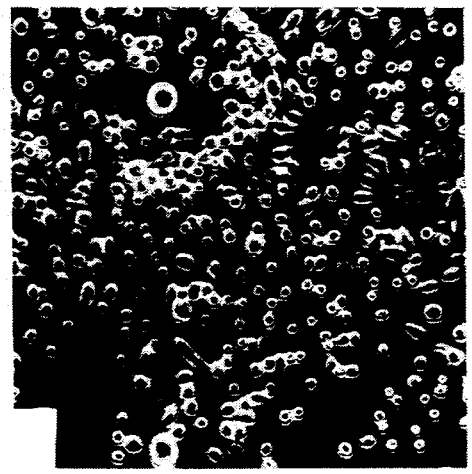
FIG. 5F is a photomicrograph similar to FIG. 5E, but taken 60 minutes after treatment with EDTA.

The ultrastructural immunolocalization studies of the BM165 antigen in keratinocyte cultures described above were complicated by a rounding and detachment behavior of the keratinocytes during long incubations with concentrated BM165 mAb. Scanning electron micrographs showing the altered morphology of the BM165-incubated cells compared to the morphology of untreated keratinocytes is shown in FIGS. 4C and 4D, respectively. The treated keratinocytes shown in FIG. 4C had become rounded and detached during incubation with BM165 mAb.

Detached keratinocytes readily re-plated onto plastic and grew with equal vigor compared to untreated cells, indicating that the rounded and detached cells were not metabolically compromised by the antibody treatment (not shown).

To further pursue these observations, just-subconfluent keratinocyte cultures were separately incubated with purified BM165 mAb for 10 and 60 minutes. After incubation, the cultures were photographed (FIGS. 5A–F). Purified mAbs in PBS, PBS alone, or 10-mM EDTA were incubated with keratinocytes in parallel. Parallel cultures were also incubated with anti-type-VII monoclonal IgG in PBS for the corresponding same length of time. BM165 mAbs (FIGS. 5C and 5D) and EDTA (FIGS. 5E and 5F) were observed to cause extensive rounding and detachment of the keratinocytes after 60 minutes' incubation. Such rounding and detachment were not observed when the cultures were incubated with PBS (FIGS. 5A and 5B), anti-type-VII collagen nor anti-laminin (not shown). Dermal fibroblasts were rounded and detached by EDTA but not by BM165 (not shown). Therefore, the BM165 epitope is involved in keratinocyte attachment, but not in the attachment of dermal fibroblasts to substrates.

The photomicrographs in FIG. 3A also indicate that confluent keratinocyte cultures exhibit no intracellular fluorescence. To evaluate substrate deposition of the antigen occurring relative to the time of plating, keratinocytes were plated at low density, and the development of fluorescence was observed as a function of increasing cell density.

Photomicrographic results of these studies are shown in FIGS. 6A–6E, and demonstrate that synthesis of the BM165 antigen correlated with growing and migrating cells. At six hours after plating, only intracellular fluorescence was observed (FIG. 6A). By 24 hours, individual cells and cell clusters exhibited both perinuclear intracellular fluorescence and fluorescent staining of the substrate immediately adjacent the cells (FIGS. 6B, 6D and 6E). In some cases, cells appeared to have migrated, leaving behind fluorescent stain attached to the substrate (FIGS. 6D and 6E). As the cell clusters enlarged (FIG. 6C), only the peripheral cells demonstrated intracellular fluorescence, showing that cells situated in the center regions of the clusters were no longer synthesizing this antigen. These results are consistent with previous observations that cell growth and migration occur at the periphery of keratinocyte colonies and internal cells are quiescent. Barrandon et al., *Cell* 50:1131–1137 (1987). Since the interior cells of confluent cultures did not appear to synthesize the BM165 antigen, we concluded that the BM165 antigen is produced primarily by growing and migrating cells.

These data show that, in developing or regenerating epithelia, kalinin is initially distributed uniformly upon the migration substrate, then becomes reorganized to the intracellular borders upon maturation of the attachment complex. This is supported by the observation that keratinocytes cultured either on plastic or glass deposit kalinin uniformly upon the substrate, not solely beneath what appear in culture to be immature hemidesmosomes. Once cultures of keratinocytes have become confluent and have a sufficient surface to be grafted on a patient, the confluent culture has stopped depositing kalinin on the substrate. This is believed to account for the poor adhesion of cultured keratinocytes to the dermis, muscle or subcutaneous tissue of a skin graft site.

10. PAGE of Kalinin

Figure 7:
FIG. 7 is a Western blot showing an electrophoretic analysis of the BM165 antigen isolated from keratinocyte culture medium.

To further characterize the antigen, the BM165 immunogen was fractionated from keratinocyte medium by immunoaffinity chromatography using BM165 mAbs, and was analyzed by polyacrylamide gel electrophoresis (FIG. 7). As described above (see, Immunogen Purfication) the BM165 antigen was affinity-purified from spent keratinocyte culture medium. When analyzed by sodium dodecyl sulfate-polyacrylamide gel electrophoresis (SDS-PAGE) before disulfide reduction, two species were visualized by staining with Coomassie Blue (lane 1). Both molecular species were immunoblot positive (lane 2). The predominant species migrated with an estimated $M_r$ of approximately 400,000 daltons, and a minor species of $M_r$ 440,000 daltons was often seen.

After disulfide bond reduction with mercaptoethanol, four major electrophoretic species were resolved (lane 3, arrows): $M_r$=165,000, 155,000, 140,000 and 105,000 daltons. None of these bands were immunoreactive with polyclonal antiserum to EHS laminin (Sigma), or with monoclonal antibodies to human A, B1 or B2 chains (Engvall) (data not shown). Only the 165-kDa (kilodalton) species (and an immunoreactive smaller species that does not correspond to any of the chemically stained bands and is presumed to be a degradation product) contains the BM165 epitope as shown by Western blot when probed with mAb BM165 (lane 4).

The disulfide bonded 400-kDa and 440-kDa species were separately excised from the gel and reduced with 2-mercaptoethanol. The reduction products were separated electrophoresis. The 400-kDa species included the 165-kDa, 155-kDa and 140-kDa chains (lane 5) and a small amount of a 200-kDa species seen only faintly after staining with Coomassie blue (lane 3). The 200-kDa species also included the BM165 epitope. The 400-kDa species included the 165-kDa, 140-kDa and 105-kDa chains (lane 7). These results are consistent with identification of a protein molecule having three non-identical chains.

The differences in the electrophoretic mobilities of the non-reduced species can be explained by a conversion of the 155-kDa species to a 105-kDa species by proteolysis.

The results also showed that the 165-kDa and 200-kDa chains bear a precursor-product relationship, as confirmed by biosynthetic pulse-chase experiments. It is not clear if these proteolytic events are physiological.

11. Rotary Shadowing of Kalinin

Rotary-shadow imaging of the purified BM165 antigen revealed a linear molecule comprising a central rod 107 nm long (FIG. 8)A. The molecule is seen in two forms. The more common form appears to have an extended dumbbell-shaped profile (FIG. 8B), FIG. 8C and FIG. 8D with a globular knob at each terminus of the rod. One knob often appears smaller than the other. The lesser abundant form is asymmetric, with a large globule at one end and two smaller globules at the other FIG. 8E, FIG. 8F and FIG. 8G, in particular FIGS. 8F and 8G. Both forms are different from any other molecules of which the inventors are aware. The relative abundance of the two forms, and the presence of an additional knob on the larger species, is consistent with the larger image being representative of the 440-kDa form.

Rotary shadowing of kalinin indicates that it is an asymmetric molecule. This confirmation is consistent with a molecular structure in which one site on kalinin molecules is capable of interaction with receptors on the keratinocyte surface and another part remains buried within the lamina densa, thus providing cell-substrate adhesion. This impression is further supported by the observed disruption of cell-substrate contact upon incubation of cultured cells with the antibody, and the consistent and dramatic de-epithelization of skin caused by the BM165 antibody.

12. Precursor-Product Relationships of Kalinin

We show here that a high-molecular-weight (HMW) form of kalinin is secreted by keratinocytes and is processed extracellularly to lower-molecular-weight forms. The extracellular processing appears to involve two independent steps.

Referring to FIG. 10A, three forms of kalinin are present following immunoprecipitation of radiolabeled keratinocyte cultures using BM165 mAbs. In the experiment shown in FIG. 10A, cultures of keratinocytes were metabolically labeled in medium containing 0.035 mM $CaCl_2$ (lane 2), 0.15 mM $CaCl_2$ (lanes 1 and 3), or 1.0 mM $CaCl_2$ (lane 4), for 24 hours after attachment. Labeled cells (lane 1 and medium (lanes 2, 3, 4) were immunoprecipitated with BM165 mAb, separated by non-reduced SDS-PAGE on 3–5% gradient acrylamide gels, and visualized by fluorography. Selected radioactive bands were excised from the dried gel, and rehydrated in gel sample buffer containing 2% 2-mercaptoethanol.

One form of kalinin, present in the cell fraction, is termed "KC" and is estimated to be about 460 kDa by non-reduced SDS-PAGE (lane 1). Two other forms, termed "KM1" (440 kDA) and "KM2" (400 kDa), are observed in media fractions (lanes 2, 3, and 4). KM1 mainly accumulates in the medium of keratinocytes cultured under conditions of low calcium concentration (0.035 mM $CaCl_2$, lane 2). KM2 mainly accumulates in the medium of keratinocytes cultured in high-calcium medium (1.0 mM $CaCl_2$, lane 4). In medium containing 0.15 mM $CaCl_2$ (lane 3), roughly equal amounts of each of KM1 and KM2 accumulate during culturing.

Figure 10B:
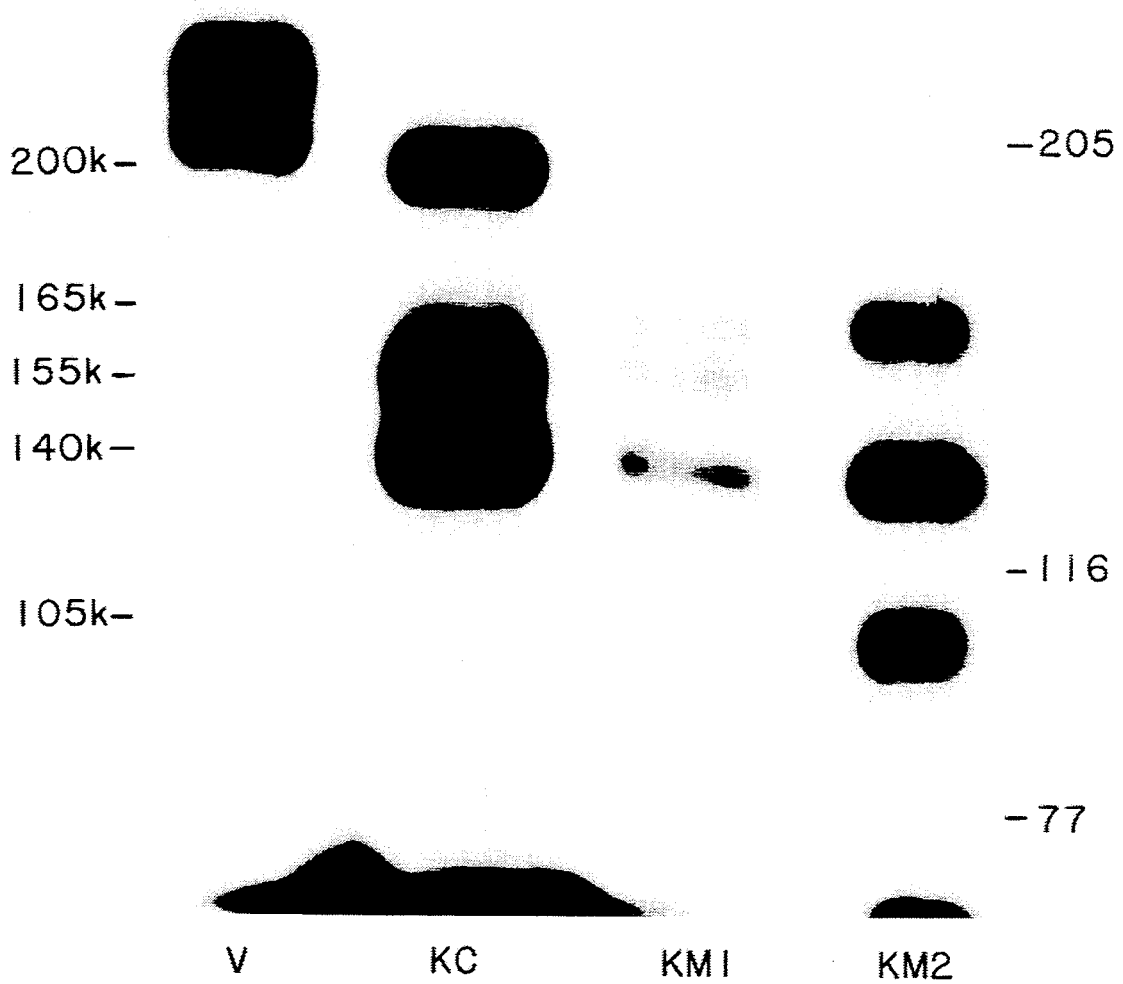

In addition to kalinin, BM165 mAbs co-precipitate a 650-kDa protein from keratinocyte medium (indicated by the "V" symbol in FIG. 10A, lanes 2–4). The 650-kDa form is a novel variant of laminin comprising, when subjected to second-dimension reduction, laminin B1 and B2 subunits and a unique 190-kDa subunit (FIG. 10B, lane 1).

In FIG. 10B, reduced samples were separated by SDS-PAGE on 5% acrylamide gels. Samples were as follows: reduced laminin variant V (lane 1); reduced kalinin form KC (lane 2); reduced kalinin form KM1 (lane 3); and reduced kalinin form KM2 (lane 4). Markers on the right indicate positions of the reduced kalinin subunits. Markers to the right represent $M_r \times 10^{-3}$.

After gel-purification, KC, KM1, and KM2 bands similar to those shown in FIG. 10A (lanes 1 and 3) were excised and subjected to second-dimension reduction analysis (FIG. 10B, lanes 2–4, respectively). All three forms of kalinin were found to include a 140-kDa subunit. KC, but not KM1 or KM2, also included a 200-kDa subunit. KC also included a 155-kDa subunit. KM1 included, in addition to the 140-kDa subunit, a 165-kDa subunit and a 155-kDa subunit. KM2 included, in addition to the 140-kDa subunit, a 165-kDa and a 105-kDa subunit. These results indicate that KC is converted to KM1 wherein the 200-kDa subunit is processed to 165-kDa, and that KM1 is converted to KM2 wherein the 155-kDa subunit is processed to the 105-kDa.

Figure 11:
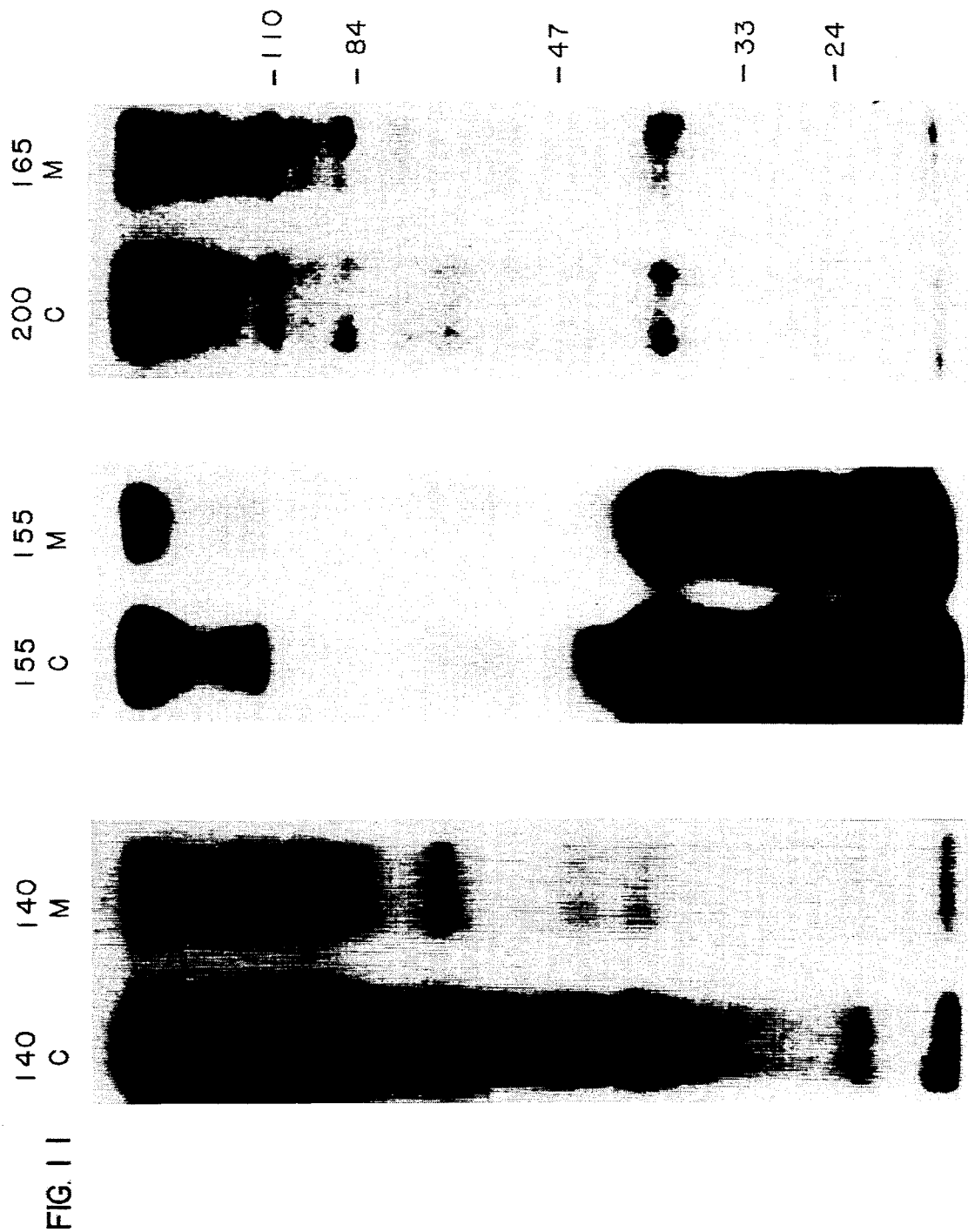
FIG. 11 comprises peptide fragmentation maps of kalinin subunits obtained after digestion with Staphylococcal V8 protease.

FIG. 11 depicts peptide fragmentation maps of kalinin subunits obtained following digestion with Staphylococcal V8 protease. Cultures of keratinocytes growing in medium containing 0.15 mM $CaCl_2$ were metabolically labeled for 24 hours, immunoprecipitated with BM165 as in FIGS. 10A–10B, and separated by reduced SDS-PAGE on 5% acrylamide gels. Radioactive bands containing the reduced kalinin subunits of the indicated molecular weight were excised from the dried gels and partially digested with V8 protease. Digestion products were separated by SDS-PAGE on 10% acrylamide gels and visualized via fluorography. The right margin indicates $M_r \times 10^{-3}$.

When subjected to such V8-protease peptide mapping, the 140-kDa subunit of KC exhibited digestion fragments similar to digestion fragments obtained with the 140-kDa subunits of KM1 and KM2 (FIG. 11). Likewise, the 155-kDa subunit of KC exhibited a digestion pattern similar to the digestion pattern of the 155-kDa subunit of KM1. Thus, it appears that the 155-kDa subunits are not processed when KC is being converted into KM1. In addition, V8-protease digestion of the 200-kDa subunit of KC and the 165-kDa subunits of KM1 and KM2 show several electrophoretically similar fragments, indicating that the 165-kDa subunits of KM1 and KM2 are derived from the 200-kDa subunit of KC.

Comparative Western blotting studies were performed to further elucidate the processing of KC to KM1 and KM2. Results are shown in FIG. 12, showing a comparison of cell-associated, medium-associated, and tissue-associated forms of kalinin identified by Western blotting. Kalinin from SCC-25 medium fractions (lanes 1, 3, 6, and 9), cell fractions (lane 5) and from collagenase-digested human amnion (lanes 2, 4, 7, and 10) was solubilized within minutes of delivery with sample buffer containing 2-mercaptoethanol for 3 minutes at 95° C. (lane 8). All samples were then separated by reduced SDS-PAGE on 5% acrylamide gels, transferred to nitrocellulose, and stained for total protein with amido black (lanes 1, 2) or incubated in the following primary antibodies: mAb 6F12 (lanes 3, 4), polyclonal antiserum against kalinin (lanes 5, 6, 7, 8), and mAb BM165 (lanes 9, 10), then visualized with the appropriate HRP-conjugated second antibody. The right margin indicates $M_r \times 10^{-3}$.

To perform these studies, we obtained kalinin from SCC-25 squamous cell carcinoma cells (ATCC #CRL1628). Cell-associated kalinin was obtained from 80-percent confluent cultures of SCC-25 cells grown on 100-mm diameter plastic culture dishes. The cell layers were washed with PBS, then extracted with ice-cold lysis buffer (10-mM Tris-HCl pH 7.4, 150-mM NaCl, 2-mM EDTA, 250-μM PMSF, 1 mM n-ethylmaleimide, 0.3% NP-40, 0.05% Triton X100, 0.3% sodium deoxycholate, 0.1% BSA, and 0.1% SDS). All subsequent steps were performed at 4° C. Cells and matrix were removed from the dishes using a cell lifter, then solubilized with a Dounce homogenizer and centrifuged at 25,000×g for 30 minutes. The supernatant was treated with diisopropyl fluorophosphate (5 μg/mL), combined with K140-Sepharose, and incubated overnight on a rocking platform. The matrix was transferred to a chromatography column, washed with 50 column volumes of lysis buffer, then 50 column volumes of PBS. The column was then eluted with 1-M acetic acid. Peak fractions were determined by UV absorbance at 280 nm, pooled, dialyzed against water, then lyophilized.

To separate kalinin-like polypeptides from the culture medium bathing the cells, K140-Sepharose was employed rather than BM165-Sepharose.

Immunogen necessary to prepare "K140" mAbs was purified from human amnion. Collagenase-extracted human amnionic membranes were processed by a procedure adapted from Bachinger et al., *J. Biol. Chem.* 256:10095–10101 (1990). Proteins were precipitated from the initial soluble fraction by the addition of ammonium sulfate to a final concentration of 30% (w/v) and incubated overnight at 4° C. Precipitated materials were recovered following centrifugation (17,000×g, 60 minutes) and resuspended in chromatography buffer prior to dialysis, which greatly decreased the overall viscosity of the sample, presumably due to the removal of nucleic acids. Remaining insoluble material was removed from the sample by ultracentrifugation (18,000 rpm, 1 hour) in a Beckman Type 19 rotor. The resulting immunogen was used to inoculate two Balb/C mice. Hybridomas were prepared and screened initially by indirect immunofluorescent microscopy according to Sakai et al., *J. Biol. Chem.* 103:1577–1586 (1986). One hybridoma named "K140" produced a mAb that specifically recognized the 140-kDa subunit of kalinin.

Referring further to FIG. 12, total protein (stained with amido black) from peak-elution fractions of SCC-25 culture medium passed through the K140-Sepharose column is shown in lane 1. The pattern of bands representing kalinin subunits in lane 1 is similar to the pattern of kalinin-subunit bands purified from normal foreskin keratinocytes described hereinabove.

Lane 2 of FIG. 12 shows similarly stained total protein in peak-elution fractions from collagenase-solubilized amnionic tissue. This pattern indicates that K140 mAbs precipitate, from amnionic tissue, peptides of 220 kDa, 210 kDa, and 190 kDa (in addition to kalinin) that originate from the 650-kDa laminin variant described above. The K140-Sepharose column did not immunopurify the 650-kDa laminin variant from culture medium (FIG. 12, lane 1). These findings are believed to be not due to a cross-reactivity of K140 mAb with the 650-kDa laminin variant but rather to a covalent association between kalinin and the 650-kDa laminin variant in tissue.

The K140 mAb specifically recognized the 140-kDa subunit of kalinin. The electrophoretic position of the 140-kDa subunit was unchanged in kalinin obtained from cell-culture medium (FIG. 12, lanes 3 and 6), and in kalinin obtained from tissue (lanes 4, 7, and 8). Additionally, the 140-kDa subunit of KC kalinin, recognized by a polyclonal antiserum to kalinin (lane 5), exhibited an unchanged electrophoretic behavior. The 140-kDa subunit was also recognized by K140 mAbs in reduced immunoblot analyses (data not shown). These results indicated that the 140-kDa subunit is not processed.

Referring further to FIG. 12, immunoblots of kalinin obtained from cells (lane 5), culture medium (lane 6), and tissue (lanes 7 and 8) using polyclonal anti-kalinin antiserum revealed a total of six bands. Bands representing 155-kDa and 105-kDa subunits were not identified by K140 as a product of the 140-kDa subunit (lanes 3 and 4) or by BM165 mAb as a processing product of the 200-kDa subunit (lanes 9 and 10). Together with the results shown in FIG. 10, these data indicate that the 105-kDa subunit is a proteolytic product of the 155-kDa subunit.

The polyclonal anti-kalinin antibody used in FIG. 12, lanes 5–8, was made to KM2 which contains the 105-kDa chain but not the 155-kDa chain. Nevertheless, this antiserum recognized the 155-kDa subunit. Thus, a precursor-product relationship between the 155-kDa and 105-kDa chains was indicated.

Kalinin as obtained from human amnionic tissue was compared with kalinin obtained from cultured SCC-25 cells. From human amnionic tissue, kalinin was purified by affinity chromatography of material obtained from collagenase-solubilized tissue, or tissue solubilized with boiling SDS-PAGE buffer. From cultured cells, kalinin was purified either from the cells or from the medium bathing the cells. Referring further to FIG. 12, the collagenase-solubilized amnion samples (lane 7) and the buffer-solubilized amnion samples (lane 8) each produced three bands immunoreactive with polyclonal anti-kalinin antibodies. These bands are equivalent to the 165-, 140-, and 105-kDa subunits of kalinin. Samples obtained from SCC-25 cells (lane 5) or cell-culture medium (lane 6) reveal the 200- and 155-kDa subunits of kalinin as recognized by polyclonal anti-kalinin antibodies. The 200- and 155-kDa subunits were apparently absent from material obtained from amnionic tissue (lanes 7 and 8). Thus, it appears that kalinin obtained from amnionic tissue is similar to the most extensively processed form of kalinin present in cell-culture medium, i.e., KM2.

Amnionic-tissue kalinin (FIG. 12, lanes 7 and 8) also produced a 145-kDa band which was stained less intensely by anti-kalinin polyclonal antibodies than other bands from such tissue. Immunoblots of the collagenase-solubilized sample performed using BM165 mAb (lane 10) indicated that the 145-kDa subunit was a proteolytic product of the 165-kDa subunit. Such proteolysis was seldom observed in cell culture.

Figure 13A:
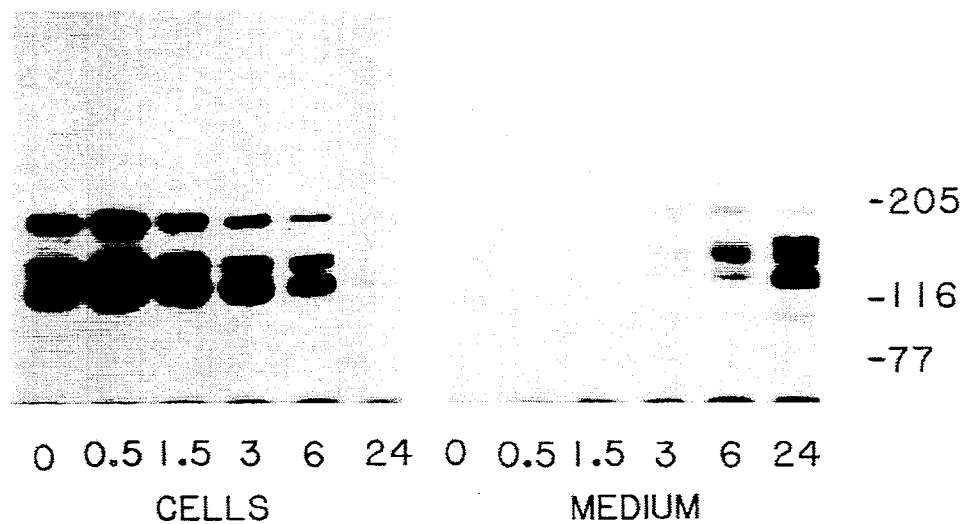
FIGS. 13A–13B show the results of pulse-chase comparisons of cell-associated and medium-associated forms of kalinin, wherein immunoprecipitated products are shown after separation on acrylamide gels.
Figure 13B:
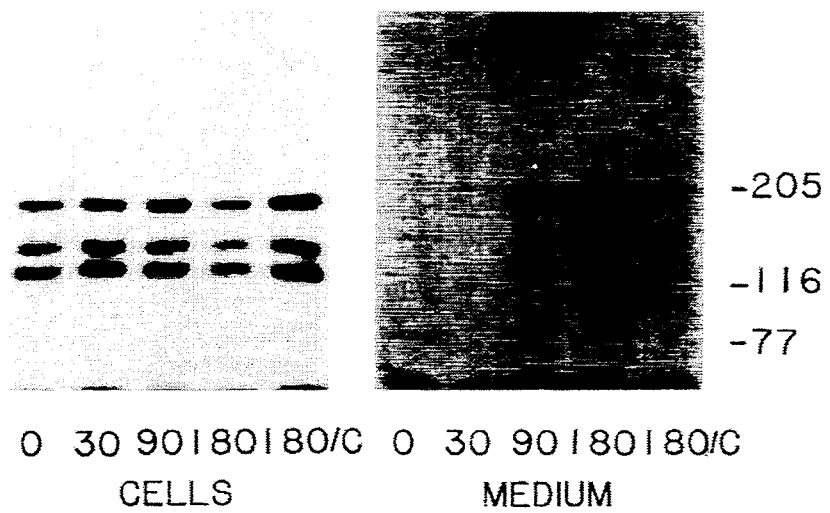

In order to determine the site, rate, and other dynamics of kalinin processing, pulse-chase experiments were performed using both suspended and attached keratinocytes. The experiments shown in FIGS. 13A–13B indicate that, with both suspended and attached keratinocytes, labeled kalinin appeared in the cell-culture medium about 90 minutes after a 10-minute pulse. FIGS. 13A and 13B show the results of pulse-chase comparisons of the cell-associated and culture-medium forms of kalinin. In FIG. 13A, attached keratinocytes were labeled in medium containing $^{35}$S-methionine and $^{35}$S-cysteine for ten minutes. Radioactive medium was removed and the cells were subsequently cultured in non-radioactive medium. Cultures were removed and the cell- and medium-fractions were processed for immunoprecipitation with polyclonal kalinin antisera after 0, 0.5, 1.5, 3, 6, and 24 hours of radioactive chase. In FIG. 13B, keratinocytes in suspension culture were labeled as in FIG. 13A. Radioactive medium was removed and the cells were cultured in non-radioactive medium for 180 minutes. Aliquots of cells and medium were removed at the end of the labeling period. After 30, 90, and 180 minutes of radioactive chase, the cells and medium were immunoprecipated with polyclonal antiserum against kalinin. Precipitated products were separated by reduced SDS-PAGE on a 5% acrylamide gel and visualized by fluorography. In one condition (180C) , cells were cultured in 10 nm colchicine during labeling and a 180-minute chase period prior to the processing of the cell and medium fractions for immunoprecipitation. The right margin indicates $M_r \times 10^{-3}$.

Thus, kalinin in the KC form is synthesized and secreted by the cells in less than 90 minutes as indicated by the appearance in the medium of the KC-derived 200-kDa band. The secretion of kalinin into the medium of suspended cultures is inhibited by 10-nM colchicine, resulting in the accumulation of the KC form within treated cells. These results show that the KC form of kalinin is secreted, not released, as a consequence of cell lysis, and that the secretion is inhibited by colchicine. Thus, the KC form is not solely an intracellular precursor to the medium forms.

A significant portion of the labeled KC form of kalinin persists in the attached cell fraction even after six hours of chase (FIG. 13A), much longer than the secretion time noted above, although it appears to significantly clear from the cell fraction by 24 hours. Conversely, the culture-medium forms of kalinin (KM1 and KM2) do not accumulate in the cell fraction in either the attached or suspended conditions (FIGS. 13A and 13B) or after a 24-hour continuous labeling of attached cells (FIG. 1). One interpretation of these results is that the KC form of kalinin remains with the cell fraction after secretion due to affinity with the culture substrate or cell component and that, during processing of the 200-kDa subunit to the 165-kDa subunit, this affinity is lost, thereby facilitating the diffusion of KM1 into the medium. These observations are consistent with other results disclosed herein showing kalinin to be extensively deposited onto the culture substratum by actively growing and migrating keratinocytes.

The 165-kDa and 105-kDa subunits are consistently absent from the cell fractions of either suspended or attached keratinocytes (FIGS. 13A–13B). These results indicate that the processing of the 200-kDa subunit to a 165-kDa subunit and the processing of the 155-kDa subunit to the 105-kDa subunit occur extracellularly. The appearance of the 165-kDa subunit in medium of suspended and attached keratinocytes occurs at 90 minutes, suggesting that the processing of the 200-kDa subunit to the 165-kDa subunit begins shortly after secretion. The 200-kDa subunit band in the medium of the attached cells is diminished in intensity and the 165-kDa subunit is increased in intensity after 24 hours compared to after six hours of radioactive chase. In contrast, the 105-kDa subunit appears in culture medium only after a radioactive chase period of between six and 24 hours, indicating that the extracellular processing of the 155-kDa subunit to 105 kDa occurs at a much slower rate compared to the first processing step.

Figure 14:
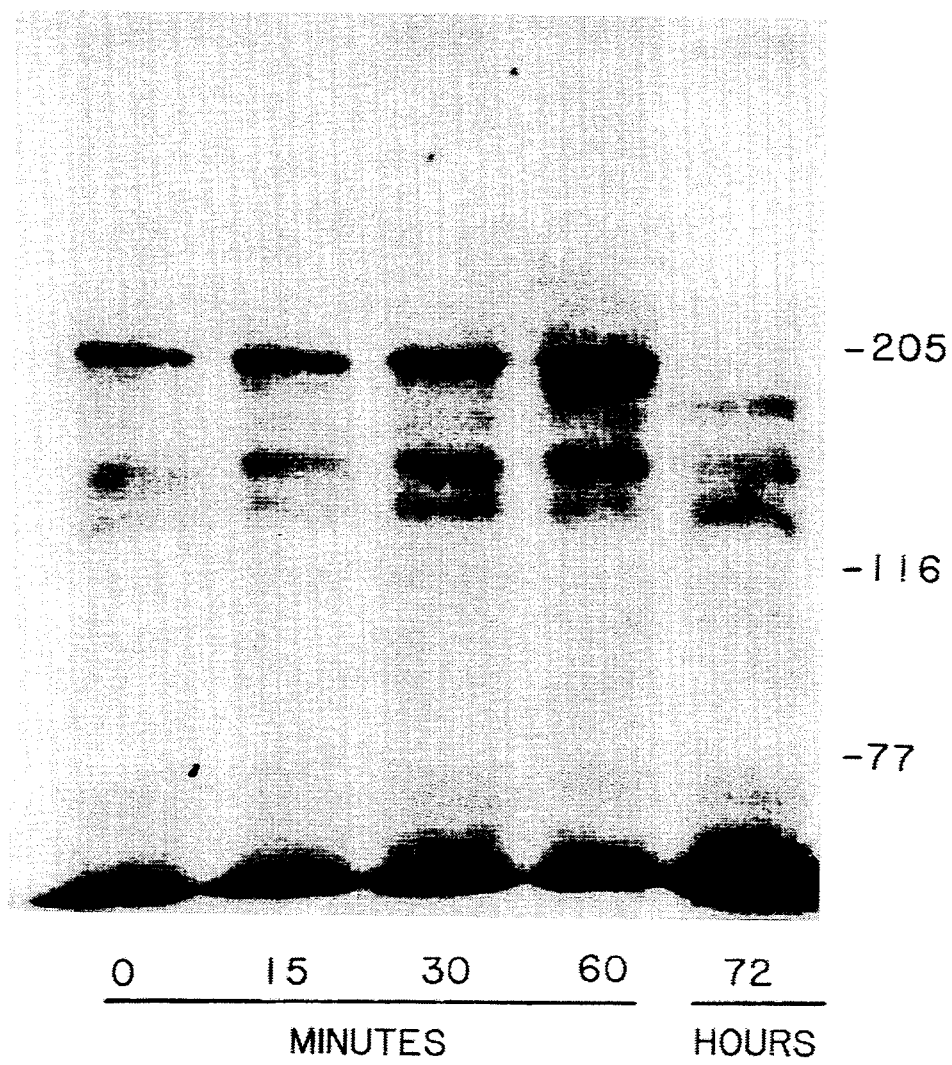
FIG. 14 shows the results of a pulse-chase comparison of kalinin synthesized by organ-cultured bovine skin, wherein immunoprecipitated products are shown after separation on acrylamide gels.

To further characterize the biosynthetic data obtained from primary cell culture with processing events in vitro, skin organ culture pulse-chase studies were performed, as shown in FIG. 14. FIG. 14 shows a pulse-chase comparison of kalinin synthesized by organ-cultured bovine skin. Fetal bovine skin in organ culture was radiolabeled in medium containing $^{35}$S-methionine and $^{35}$S-cysteine for 10 minutes (lanes 1, 2, 3, 4) or for 16 hours (lane 5), then cultured in non-radioactive medium. Aliquots of cultured skin were removed at the end of the labeling period (lane 1) and after radioactive chase, immunoprecipated with polyclonal antiserum against kalinin, separated by reduced SDS-PAGE on a 5% acrylamide gel, and visualized by fluorography. The right margin indicates $M_r \times 10^{-3}$.

At the onset of organ culture, after a ten-minute radioactive pulse, only the KC form of kalinin was detected (FIG. 14, lanes 1–4). After a prolonged period of radioactive chase, the 200-kDa subunit was apparently completely converted to 165 kDa (lane 5). Both the 155- and 140-kDa subunits were present after 72 hours' chase. During this period, there was no observed conversion of the 155-kDa subunit to 105 kDa, either because no processing occurred, or because KM2 in tissue is not solubilized by the immunoprecipation buffer used for the extractions.

13. Cultured Epidermal Keratinocyte Transplantation

Methods of transplanting keratinocytes have already been disclosed in the literature, and any of these methods are suitable for modification according to the present invention. Knowledge of how such transplants are generally performed is within the purview of persons skilled in the art. However, by way of illustration, several examples of suitable transplant methods are disclosed.

EXAMPLE 1

One method of keratinocyte transplantation was disclosed by O'Connor et al., *The Lancet* 1:75–78 (1981). A patient had two 2cm² skin samples removed under local anesthesia. The tissue was placed in culture medium and transferred to a laboratory for cultivation and graft preparation. As much subcutaneous tissue and dermis as possible was removed from the tissue, and the tissue was then minced and trypsinized. The cells were inoculated at different densities (from $10^4$ to $10^6$ per 50-mm diameter dish containing $4 \times 10^5$ lethally irradiated 3T3 cells). The cultures were supplied with fortified Eagle's medium supplemented with 20% fetal calf serum, 0.4 µg/mL hydrocortisone, and 0.1 nmol/L choleragen. The cultures were incubated at 30° C. in a 10% $CO_2$ atmosphere. After three days, epidermal growth factor (EGF 10 ng/mL) was added to the culture medium. The medium was changed twice weekly until the cultures either became confluent (between 14 and 21 days) or were subcultured. Some subconfluent cultures were viably frozen and later subcultured. In this way, secondary and tertiary subcultures could be prepared for later use as grafts.

The confluent epithelial cells were detached in their confluent state from the surface of the culture dishes using the enzyme dispase. After detachment, each elastic epithelium shrank to a diameter of 2 to 2.5 cm. Each epithelium was then washed with serum-free medium and placed basal-side up on two layers of sterile vaseline gauze cut into 2-cm diameter circles. Sufficient serum-free medium was added to cover the exposed basal surface. Several dishes containing grafts were then placed in a glass jar; the atmosphere in the jar was flushed with 10% $CO_2$ and the sealed jar was transported to the bedside.

Epithelial grafts including the vaseline gauze covering were placed on prepared wound sites with the basal cell layer directed against the wound surface. No suturing was necessary because the grafts were held in place by a single layer of non-impregnated fine mesh gauze, which was overlayed with a loose layer of coarse mesh gauze that was changed daily. The fine mesh gauze and the vaseline gauze were removed between the sixth and tenth days and the area was redressed with a single layer of vaseline gauze and a loose layer of coarse gauze. These dressings were changed daily for three to four weeks from the time of grafting. Thereafter, the grafts were left exposed to the atmosphere, but treated with a thin layer of lanolin ointment once daily.

The epithelial grafts described above were placed on three different types of "recipient beds" (wound surfaces): early granulation tissue (less than 7 days old), chronic granulation tissue, and areas recently excised down to the facia.

In accordance with the present invention, adhesion of the confluent epithelium to the underlying tissue would be improved by spreading a thin layer of exogenous kalinin either on the basal face of the keratinocyte culture or on the epithelium of the exposed surface of the tissue on which the graft was being placed. Such exogenous kalinin would provide superior adhesion because (a) the confluent keratinocytes in cell culture have stopped or significantly decreased kalinin production; (b) kalinin originally present on the basal surfaces of the cultured cells was destroyed by the dispase treatment; and (c) kalinin is necessary for stabilization of the dermal-epidermal junction.

EXAMPLE 2

Methods of grafting autologous cultured human epithelium were also disclosed in Gallico et al., *New Eng. J. Med.* 311:448–451 (1984). The patients were two children who sustained burns on more than 95% of their bodies, but had half or more of their body surfaces successfully covered with cultured epithelial autografts. On admission, a 2cm² full-thickness biopsy specimen of skin was removed from the axilla of each patient. The skin was minced and trypsinized to produce a single cell suspension. Aliquots of $2 \times 10^6$ cells were frozen and stored or cultured in flasks with a surface area of 75 cm². When the colonies became confluent at 10 days, the cultures were trypsinized, and $3 \times 10^5$ cells were inoculated to make secondary and tertiary cultures for grafting. To prepare grafts, the cultured sheets of cells were released from the flasks with dispase, washed with medium, and applied to petrolatum gauze cut to $4.5 \times 6$ cm. The burn wounds had been excised to muscle fascia, except for third-degree facial burns, which were excised tangentially to a depth sufficient to remove dead tissue. The cultured grafts with their gauze backing were placed on prepared wound surfaces, sutured in place, and dressed with dry gauze. The petrolatum gauze was removed seven to ten days later.

According to the present invention, the foregoing procedure would be modified by amplifying the expression of kalinin by treatment of the released keratinocytes with a cytokine yet to be identified. Since kalinin production appears to be linked to cell proliferation, growth hormones may be possible candidates. Altered feeding schedules might also be effective.

EXAMPLE 3

Transplants of autologous cultured human epithelium can be performed as in Examples 1 and 2, above. According to the present invention, the methods would be modified by transplanting the keratinocytes while a substantial number of the cells are still actively producing kalinin. In this case, subconfluent keratinocytes would be released from the culture substrate by treatment with 10-mM EDTA. The suspended cells would be washed with growth medium and suspended in Vitrogen (Collagen Corporation, Palo Alto, Calif.) and poured onto a layer of gauze in teflon forms to produce a thin stabilized layer of single keratinocytes. The Vitrogen would be gelled by brief incubation at 37° C., and the gel would be lifted from the forms and applied to the wound bed. The transferred cells would be protected as in Examples 1 and 2.

In view of the observation that kalinin is synthesized only by dividing keratinocytes, it is important to consider the state of confluence of cells to be used for successful re-epithelialization of burn wounds. Thus, kalinin may be deficient or altered in individuals with certain blistering conditions such as junctional epidermolysis bullosa (Eady, *Clin. Exp. Dermatol.* 12:161–170 (1987)) or herpes gestationis (in Katz et al. (eds.), *Dermatology in General Medicine*, McGraw-Hill, New York, pp. 586–588 (1987)). Hence, topical application of kalinin may also be useful in treating these conditions.

EXAMPLE 4

Standard in vitro attachment assays have been performed to determine that purified kalinin facilitates keratinocyte attachment to plastic substrates. In these assays, exogenous purified kalinin or control proteins are incubated overnight with the substrate, and the plates are then washed. Unattached cells are washed away, and the remaining attached cells are quantified, as described in Aumailley et al., *Exp. Cell. Res.* 181:463–474 (1989).

EXAMPLE 5

The role of kalinin in enhancing keratinocyte attachment to a substrate is also demonstrated by treating cell sheets with dispase to release them from a plastic or glass substrate, as would be done in preparing transfer sheets to a wound bed. The sheet is then transferred to a series of plastic substrates which are coated either with kalinin or controlled proteins. The adherence of the cell sheet is evaluated morphologically to demonstrate that the sheet has superior adherence to the kalinin-coated substrate. The adherence of the sheet is also evaluated by indirect immunofluorescence using the BM165 mAb. Firmly attached cell sheets will not allow antibody penetration to the substrate surface as demonstrated by the studies of confluent keratinocyte cultures. Fluorescence beneath the cells would be observed for less firmly attached sheets.

EXAMPLE 6

This example demonstrates the phase of the cell cycle during which kalinin is synthesized by cultured keratinocytes. Single keratinocytes are plated at various times after culturing begins, and kalinin is localized immunochemically within cells or upon the substrate. Intracellular kalinin is present only within single cells or small clusters of keratinocytes. It is not found intracellularly within the keratinocytes that are in the central regions of large colonies, but only at the periphery where cells are still dividing and migrating.

Figure 15:
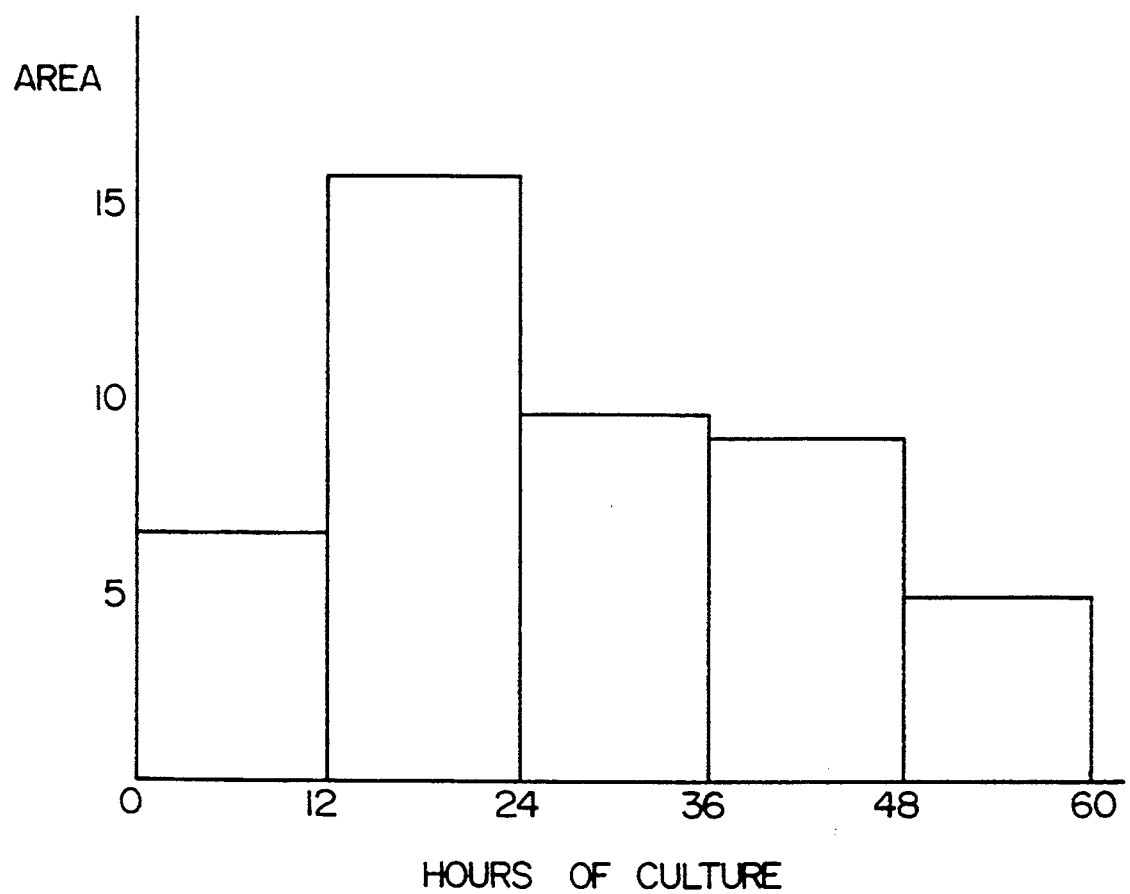
FIG. 15 is a graph of the amount of kalinin immunoprecipitated with antibody BM165 from keratinocytes radiolabed during the indicated times of culture.

At various times, cultures are incubated with radioisotopic protein precursors for twelve hours at selected times after plating. Kalinin is then quantitatively immunoprecipitated as a function of total time in culture. The preliminary results of the experiments show that kalinin synthesis decreases with time in culture when measured on a per cell basis (FIG. 15). This information will define the optimal time of cell culture to maximize kalinin production and deposition by keratinocytes.

The present invention includes kalinin from both human and animal sources. Kalinin is present in (and can be purified from) such diverse sources as fetal calf, human amnion and amniotic fluid.

In the future, technical advancements may also permit identification, isolation and purification of individual domains of kalinin which provide keratinocyte adhesion. These domains can be identified by fragmentation of isolated kalinin to produce individual domains, and individualized testing of each domain's ability to function as a keratinocyte-attachment factor. Alternatively, domain specific monoclonal antibodies that block cell adhesion could be generated and used to identify the active domain or domains. Once these advances have taken place, the isolated adhesion domains can be purified and used in the present invention.

Future advances may also permit molecular cloning of kalinin, kalinin sub-chains, or related proteins which provide keratinocyte adhesion. These cloned chains will provide structural information about the identified structural domains. The cloned domains can then be expressed in vitro. If the cell attachment domain is contained within a single kalinin chain, it is possible that a functional fragment could be produced in vitro. Recombinant protein fragments would be transfected into CV-1 cells using the SV40 virus vector as described in Kriegler et al., *Gene Transfer and Expression*, Stockton Press, New York (1990).

Having illustrated and described the principles of the invention in several preferred embodiments, it should be apparent to those skilled in the art that the invention can be modified in arrangement and detail without departing from such principles. We claim all modifications coming within the spirit and scope of the following claims.

We claim:

1. A method of improving adhesion of transplanted keratinocytes to a substrate, comprising the step of providing an amount of purified kalinin between the keratinocytes and the substrate wherein the kalinin is of molecular weight about 400 to about 460 kDa and wherein the kalinin provides adhesion between human dermis and epidermis.

2. A method of improving adhesion of transplanted keratinocytes to a substrate, comprising:
   monitoring the production of a protein kalinin by cell cultures of keratinocytes, wherein said kalinin is of molecular weight about 400 to about 460 kDa and provides adhesion between human dermis and epidermis; and
   transplanting keratinocytes while they are actively producing kalinin.

3. The method of claim 1 wherein the substrate is the surface of a burn wound.

4. The method of claim 2 wherein the substrate is the surface of a burn wound.

5. The method of claim 4 wherein the substrate is human dermis or subcutaneous tissue.

6. The method of claim 3 wherein the substrate is human dermis or subcutaneous tissue.

7. A method of improving adhesion of transplanted keratinocytes to a substrate, comprising the step of providing a sufficient amount of kalinin between the keratinocytes and the substrate, wherein the kalinin is a protein of molecular weight about 400 to about 460 kDa having the characteristic of providing adhesion between human dermis and epidermis and wherein the provided kalinin is exogenous to the transplanted keratinocytes and the substrate.

8. The method of claim 7 wherein the substrate is the surface of a burn wound.

9. The method of claim 7 wherein the substrate is human dermis or subcutaneous tissue.

* * * * *